United States Patent
Bolin et al.

(10) Patent No.: US 7,317,125 B2
(45) Date of Patent: Jan. 8, 2008

(54) DIACYLGLYCEROL ACYLTRANSFERASE INHIBITORS

(75) Inventors: David Robert Bolin, Montclair, NJ (US); Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/343,567

(22) Filed: Jan. 31, 2006

(65) Prior Publication Data

US 2006/0178532 A1    Aug. 10, 2006

Related U.S. Application Data

(60) Provisional application No. 60/650,671, filed on Feb. 7, 2005.

(51) Int. Cl.
C07C 243/14    (2006.01)
A61K 31/16    (2006.01)

(52) U.S. Cl. .................. 564/149; 514/432; 514/448; 514/451; 514/461; 514/614; 514/615; 514/616; 549/13; 549/72; 549/425; 549/487; 564/148; 564/150

(58) Field of Classification Search .............. 564/148, 564/149, 150; 514/615, 616, 432, 448, 451, 514/461; 549/13, 72, 425, 487
See application file for complete search history.

(56) References Cited

U.S. PATENT DOCUMENTS 3,439,018 A * 4/1969 Leafe et al. ............. 560/45
2004/0224997 A1 11/2004 Smith et al.

FOREIGN PATENT DOCUMENTS

| EP | 1219716 | 7/2002 |
|---|---|---|
| JP | 48-7766 | * 3/1973 |
| JP | 2004067635 | 8/2002 |
| WO | WO2004047755 | 6/2004 |

OTHER PUBLICATIONS

Abstract-XP002383264 KR 460 438 B, Korea Res Inst Bioscience & Biotechnolog, Dec. 8, 2004.
Subauste and Burant, Current Drug Targets—Immune, Endocrine & Metabolic Disorders (2003) 3, 263-270.
Mayorek et al, European Journal of Biochemistry (1989) 182, 395-400.
Farese et al, Current Opinions in Lipidology (2000) 11, 229-234.
Coleman et al, Journal of Molecular Biology (1978) 253, 7256-7261.
Yu et al, Journal of Molecular Biology (2002) 277, 50876-50884.
Colman, Methods in Enzymology (1992) 209, 98-104.
Owen et al, Biochemical Journal (1997) 323 (pt 1), 17-21.
Waterman et al, Journal of Lipid Research (2002) 43, 1555-156.
Shelness and Sellers, Current Opinions in Lipidology (2001) 12, 151-157.
Cases et al, Proceedings of the National Academy of Science, USA (1998) 95, 13018-13023.
Lardizabal et al, Journal of Biological Chemistry (2001) 276, 38862-38869.
Cases et al, Journal of Biological Chemistry (2001) 276, 38870-38876.
Smith et al, Nature Genetics (2000) 25, 87-90.
Lehner and Kuksis, Progress in Lipid Research (1996) 35, 169-210.
Chen and Farese, Trends in Cardiovascular Medicine (2000) 10, 188-192.
Chen and Farese, Current Opinions in Clinical Nutrition and Metabolic Care (2002) 5, 359-363.
Chen et al, Journal of Clinical Investigation (2002) 109, 1049-1055.
Buhman et al, Journal of Biological Chemistry (2002) 277, 25474-25479.
Kahn, Nature Genetics (2000) 25, 6-7.
Yanovski and Yanovski, New England Journal of Medicine (2002) 346, 591-602.
Lewis et al, Endocrine Reviews (2002) 23, 201.
Brazil, Nature Reviews Drug Discovery (2002) 1, 408.
Malloy and Kane, Advances in Internal Medicine (2001) 47, 111.
Yu and Ginsberg, Annals of Medicine (2004) 36, 252-261.
S.R. Smith, Current Drug Targets CNS Neurol Disord. Oct. 2004;3(5):431-9.
Burrows et al, 26th National Medicinal Chemistry Symposium (1998) poster C-22.
Tabata et al, Phytochemistry (1997) 46, 683-687.
Casaschi et al, Journal of Nutrition (2004) 134, 1340-1346.
Kurogi et al, Journal of Medicinal Chemistry (1996) 39, 1433-1437.
Goto, et al, Chemistry and Pharmaceutical Bulletin (1996) 44, 547-551.
Ikeda, et al, Thirteenth International Symposium on Atherosclerosis (2003), abstract 2P-0401.

(Continued)

*Primary Examiner*—Shailendra Kumar
(74) *Attorney, Agent, or Firm*—George W. Johnston; Dennis P. Tramaloni; Samuel H. Megerditchian

(57) ABSTRACT

Provided herein are compounds of the formula (I):

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

24 Claims, No Drawings

OTHER PUBLICATIONS

Colman et al, Biochimica et Biophysica Acta (1992) 1125, 203-9.
Mayorek and Bar-Tana, Journal of Biological Chemistry (1985) 260, 6528-6532.
Noriko et al, (Journal of Antibiotics (1999) 52, 815-826.
Tomoda et al, Journal of Antibiotics (1995) 48, 942-7.
Chung et al, Planta Medica (2004) 70, 258-260.
Lee et al, Planta Medica (2004) 70, 197-200.
Lee et al, Journal of Antibiotics (2003) 56, 967-969.
Ko et al, Archives of Pharmaceutical Research (2002) 25, 446-448.
Zhu et al, Atherosclerosis (2002) 164, 221-228.
Ko, et al, Planta Medica (2002) 68, 1131-1133.

* cited by examiner

DIACYLGLYCEROL ACYLTRANSFERASE INHIBITORS

PRIORITY TO RELATED APPLICATIONS

This application claims the benefit of U.S. Provisional Application No. 60/650,671, filed Feb. 7, 2005, which is hereby incorporated by reference in its entirety.

FIELD OF THE INVENTION

The invention relates to inhibitors of diacylglycerol acyltransferase. The inhibitors include, for example, phenoxy- and thiophenoxyacetamide derivatives and are useful for the treatment of diseases such as obesity, type II diabetes mellitus and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver and adipocytes. Triglycerides or triacylglycerols support the major functions of dietary fat absorption, packaging of newly synthesized fatty acids, and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT were cloned and designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Further, although both enzymes are widely expressed, differences exist in the relative abundance of DGAT1 and DGAT2 expression in various tissues.

The gene encoding mouse DGAT1 has been used to create DGAT knock-out mice. These mice, although unable to express a functional DGAT enzyme (Dgat–/– mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat–/– mice are resistant to diet-induced obesity and remain lean. When fed a high fat diet, Dgat–/– mice maintain weights comparable to mice fed a diet with regular fat content. Dgat–/– mice also have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat–/– mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, are implicated in the pathogenesis of a variety of diseases. These diseases include, for example, obesity, insulin resistance syndrome, type II diabetes, metabolic syndrome (syndrome X) and coronary heart disease (see Kahn, Nature Genetics (2000) 25, 6-7; Yanovski and Yanovski, New England Journal of Medicine (2002) 346, 591-602; Lewis et al, Endocrine Reviews (2002) 23, 201; Brazil, Nature Reviews Drug Discovery (2002) 1, 408; Malloy and Kane, Advances in Internal Medicine (2001) 47, 111; Subauste and Burant, Current Drug Targets—Immune, Endocrine & Metabolic Disorders (2003) 3, 263-270; Yu and Ginsberg, Annals of Medicine (2004) 36, 252-261); and S. R. Smith, Current Drug Targets CNS Neurol Disord. October 2004; 3(5):431-9).

Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635) and substituted aryl alkyl acid (see Smith et al, US20040224997A1).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133).

A need exits in the art, however, for additional DGAT inhibitors that have efficacy for the treatment of metabolic disorders such as, for example, obesity, type II diabetes mellitus and metabolic syndrome. Further, a need exists in the art for DGAT inhibitors having $IC_{50}$ values less than about 1 μM.

SUMMARY OF THE INVENTION

In an embodiment of the present invention, a compound of the formula (I) is provided:

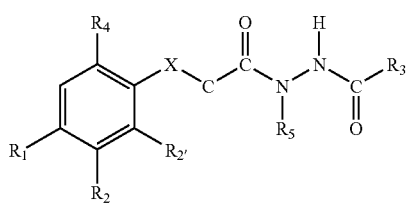

(I)

wherein: X is O or S; $R_1$ is hydrogen, halogen, ($C_1$-$C_6$)alkyl or cyano; $R_2$, $R_{2'}$ are independently of each other H or halogen; $R_3$ is unsubstituted phenyl, substituted phenyl with a group independently selected from the group consisting of halogen, ($C_1$-$C_6$) alkyl, $NH(CH_2)_nCH(CH_3)_2$, or —$O(CH_2)_n$ $OCH_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocyclyl substituted with ($C_1$-$C_6$) alkyl, or substituted or unsubstituted 5-10-membered carboxylic ring; $R_4$ is branched or unbranched ($C_2$-$C_6$) alkyl, unsubstituted phenyl, substituted phenyl which is phenyl mono-, di- or tri-substituted with a group independently selected from the group consisting of halogen, ($C_1$-$C_6$) alkyl, ($C_1$-$C_6$) alkoxy, —$O(CH)(CH_3)_2$, —$CF_3$, —$O(CH_2)_nCH_3$, —$OCF_3$, —$SCH_3$, —$SO_2CH_3$, —$NO_2$, —$(CH)_2Ar$, or unsubstituted or substituted 5-10 membered carboxylic ring; $R_5$ is ($C_1$-$C_6$) alkyl or —$CH(CH_3)_2$; n is 0, 1, 2 or 3, or a pharmaceutically acceptable salt thereof.

In another embodiment of the present invention, a method for the treatment of obesity, type II diabetes or metabolic syndrome in a patient in need thereof is provided, the method having the steps of administering to said patient a therapeutically effective amount of a compound of the formula (I):

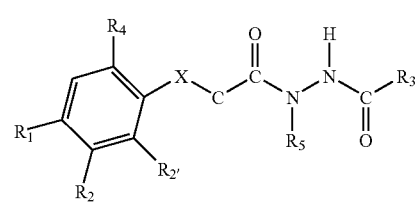

(I)

wherein: X is O or S; $R_1$ is hydrogen, halogen, ($C_1$-$C_6$)alkyl or cyano; $R_2$, $R_{2'}$ are independently of each other H or halogen; $R_3$ is unsubstituted phenyl, substituted phenyl with a group independently selected from the group consisting of halogen, ($C_1$-$C_6$) alkyl, $NH(CH_2)_nCH(CH_3)_2$, or —$O(CH_2)_n$ $OCH_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocyclyl substituted with ($C_1$-$C_6$) alkyl, or substituted or unsubstituted 5-10-membered carboxylic ring; $R_4$ is branched or unbranched ($C_2$-$C_6$) alkyl, unsubstituted phenyl, substituted phenyl which is phenyl mono-, di- or tri-substituted with a group independently selected from the group consisting of halogen, ($C_1$-$C_6$) alkyl, ($C_1$-$C_6$) alkoxy, —$O(CH)(CH_3)_2$, —$CF_3$, —$O(CH_2)_nCH_3$, —$OCF_3$, —$SCH_3$, —$SO_2CH_3$, —$NO_2$, —$(CH)_2Ar$, or unsubstituted or substituted 5-10 membered carboxylic ring; $R_5$ is ($C_1$-$C_6$) alkyl or —$CH(CH_3)_2$; n is 0, 1, 2 or 3, or a pharmaceutically acceptable salt thereof.

In a further embodiment of the present invention, a pharmaceutical composition is provided having a compound or a pharmaceutically acceptable salt or ester thereof according to the compound of formula (I) above, and a pharmaceutically acceptable carrier.

DETAILED DESCRIPTION OF THE INVENTION

The present invention pertains to DGAT inhibitors that are derivatives of, for example, phenoxy- and thiophenoxyacetamides. In a preferred embodiment, the invention provides compounds of the formula:

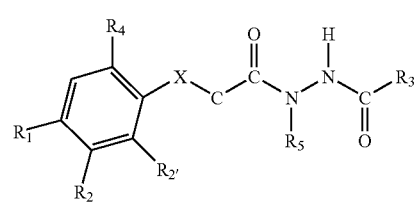

(I)

as well as pharmaceutically acceptable salts thereof.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolinyl, quinazolinyl, benzimidazolyl, benzothiazolyl, benzisoxazolyl and benzisothiazolyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such asthiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

Compounds of the present invention can be prepared beginning with commercially available starting materials and utilizing general synthetic techniques and procedures known to those skilled in the art. Outlined below are preferred reaction schemes suitable for preparing such compounds. Further exemplification is found in the specific Examples detailed below.

As shown in Scheme 1:

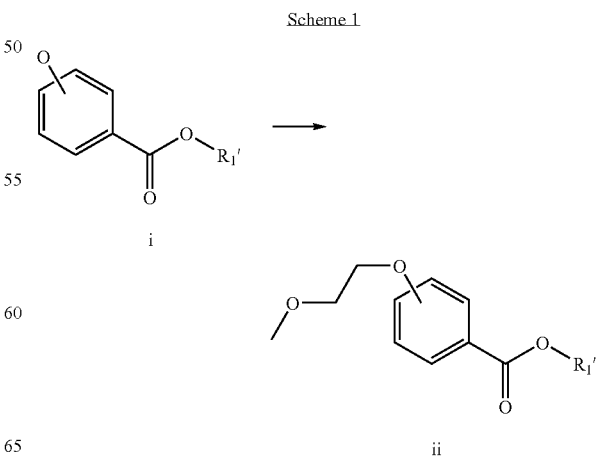

hydroxy-substituted benzoate esters i can be alkylated with 2-bromoethyl methyl ether by heating in the presence of potassium carbonate to give the alkoxy-ether substituted benzoate esters ii, where $R_1'$ is lower alkyl.

As show in Scheme 2:

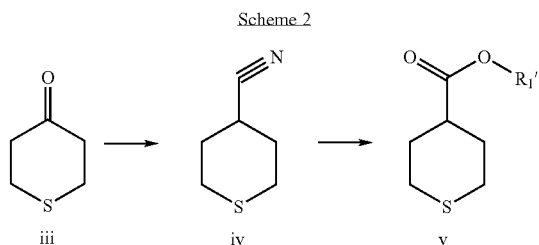

tetrahydro-2H-thiopyran-4-one iii can be treated with tosylmethylisocyanide and potassium t-butoxide in t-butyl alcohol (6.61 g, 33.8 mmol) in an appropriate solvent to yield the nitrile iv. Nitrile iv can be treated with hydrogen chloride gas in a lower alkyl alcohol solution to yield ester v, where $R_1'$ is lower alkyl.

Additionally, as shown in Scheme 3,

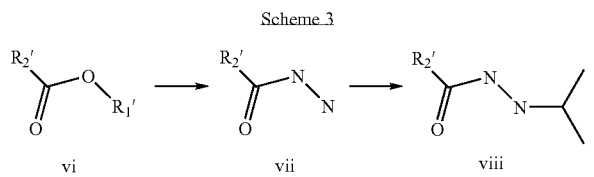

esters vi, where $R_1'$ is lower alkyl and $R_2'$ is aryl, substituted aryl, heteroaryl, substituted heteroaryl, cycloalkyl or cycloheteroalkyl can be treated with hydrazine monohydrate in an appropriate solvent with heating to yield hydrazide vii. Hydrazide vii can be dissolved in acetone, heated and then concentrated to dryness. The residue can be dissolved in and treated with triethylsilane, with warming, to yield alkyl hydrazide viii, where $R_2'$ is aryl, substituted aryl, heteroaryl, substituted heteroaryl, cycloalkyl or cycloheteroalkyl.

As shown in Scheme 4:

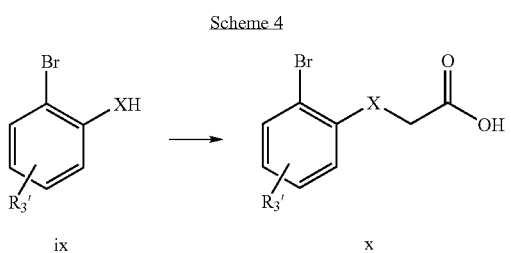

a substituted bromo-benzene ix, where X is O or S and $R_3'$ is H, halogen, cyano or lower alkyl, in an appropriate solvent can be treated with triethylamine and t-butyl bromoacetate. The intermediate can then be treated with a solution of hydrochloric acid in an appropriate to yield to yield x, where $R_3'$ is H, halogen, cyano or lower alkyl.

As shown in Scheme 5:

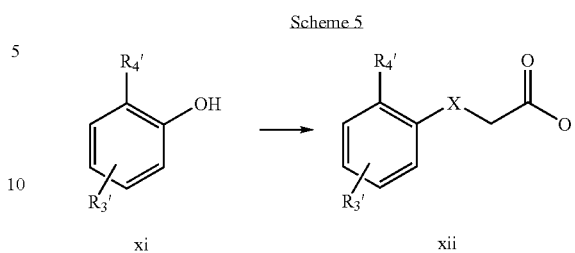

a substituted phenol xi, where $R_3'$ is H, halogen, cyano or lower alkyl and $R_4'$ is H, lower alkyl, cycloalkyl, arylalkyl, can be alkylated with t-butyl bromoacetate and potassium carbonate in an appropriate solvent. The resultant material can be treated with hydrochloric acid in an appropriate solvent to yield the aryloxy acetic acid xii.

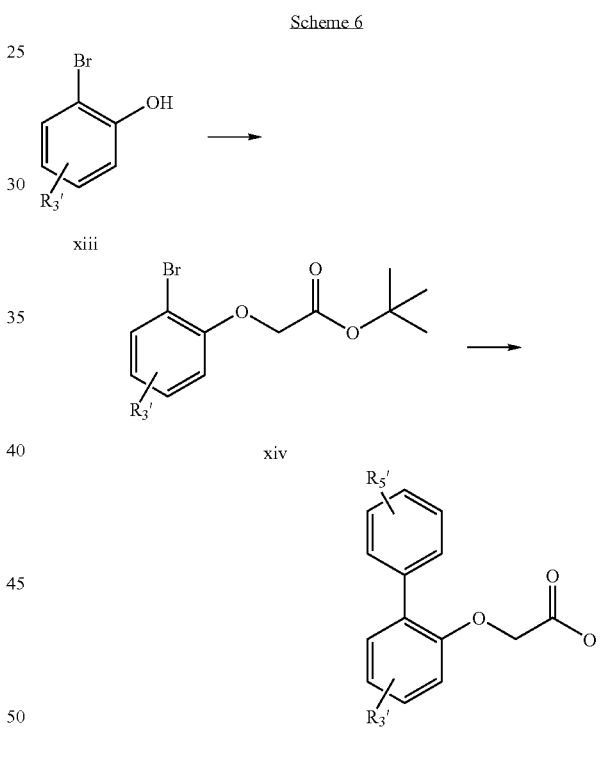

a substituted-bromo-phenol xiii, where $R_3'$ is H, halogen, cyano or lower alkyl, can be alkylated with t-butyl bromoacetate and potassium carbonate in an appropriate solvent with heating to yield t-butyl ester xiv. Using standard palladium catalyzed "cross coupling" procedures, xiv can be heated with a commercially available substituted arylboronic acid in the presence of a base, typically an aqueous solution of sodium carbonate in an appropriate solvent, typically, DME, DMF or toluene, with a catalytic amount of palladium, typically $Pd[PPh_3]_4$, to yield xv, where $R_5'$ is H, halogen, lower alkyl, nitro, alkoxy, thioalkoxy, haloalkoxy, lower alkyl carboxylate, or alkyl sulfonyl.

As shown is Scheme 7:

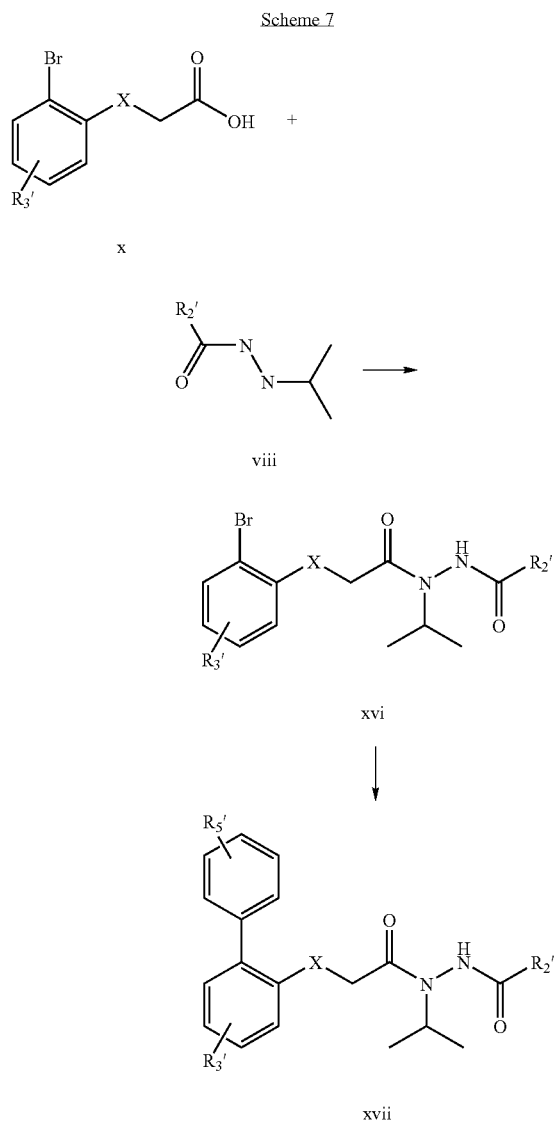

Further, as shown in Scheme 8:

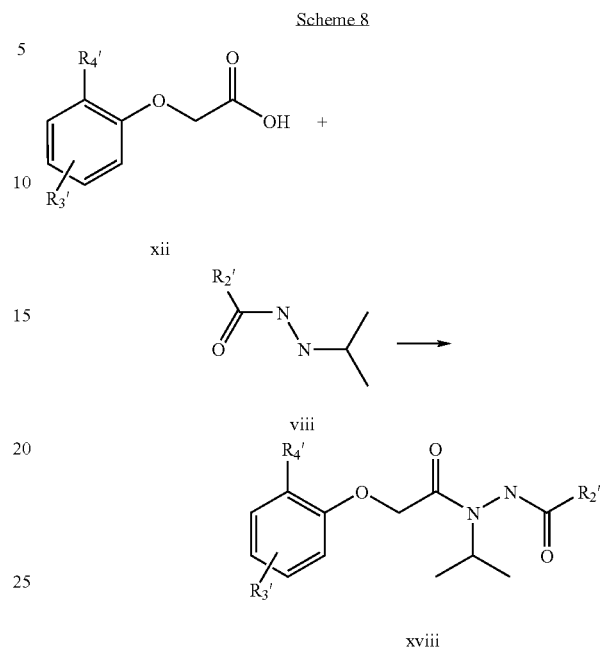

a substituted acetic acid x, where X is O or S and $R_3'$ is H, halogen, cyano or lower alkyl from Scheme 4 can be used to acylate a hydrazide viii from Scheme 3, where $R_2'$ is aryl, substituted aryl, heteroaryl, substituted heteroaryl, cycloalkyl or cycloheteroalkyl. Various standard amide bond forming conditions, as practiced by those skilled in the art, may be used. Typically, x and viii, in an appropriate solvent, may be treated with a base, such as triethyl amine, and PyBroP or ECDI and HOBT to yield acyl hydrazide xvi. Using standard palladium catalyzed "cross coupling" procedures, the arylbromide xvi can be heated with a commercially available substituted arylboronic acid in the presence of a base, typically an aqueous solution of sodium carbonate in an appropriate solvent, typically, DME, DMF or toluene, with a catalytic amount of palladium, typically $Pd[PPh_3]_4$, to yield xvii, where $R_5'$ is H, halogen, lower alkyl, nitro, alkoxy, thioalkoxy, haloalkoxy, lower alkyl carboxylate, or alkyl sulfonyl.

a substituted phenoxy-acetic acid xii, from Scheme 5, where $R_3'$ is H, halogen, cyano or lower alkyl and $R_4'$ is H, lower alkyl, cycloalkyl, arylalkyl, can be used to acylate a hydrazide viii from Scheme 3, where $R_2'$ is aryl, substituted aryl, heteroaryl, substituted heteroaryl, cycloalkyl or cycloheteroalkyl. Various standard amide bond forming conditions, as practiced by those skilled in the art, may be used. Typically, x and viii, in an appropriate solvent, may be treated with a base, such as triethyl amine, and PyBroP or ECDI and HOBT to yield acyl hydrazide xviii.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 10 to about 1000 mg per day.

The invention will now be further described in the Examples below, which are intended as an illustration only and do not limit the scope of the invention.

EXAMPLES

General Methods: Melting points were taken on a Thomas-Hoover apparatus and are uncorrected. Optical rotations were determined with a Perkin-Elmer model 241 polarimeter. 1H-NMR spectra were recorded with Varian XL-200, Mercury-300 or Unityplus 400 MHz spectrometers, using tetramethylsilane (TMS) as internal standard. Electron impact (El, 70 ev) and fast atom bombardment (FAB) mass spectra were taken on VG Autospec or VG 70E-HF mass spectrometers. Silica gel used for column chromatography was Mallinkrodt SiliCar 230-400 mesh silica gel for flash chromatography; columns were run under a 0-5 psi head of nitrogen to assist flow. Thin layer chromatograms were run on glass thin layer plates coated with silica gel as supplied by E. Merck (E. Merck #1.05719) and were visualized by viewing under 254 nm UV light in a view box, by exposure to I2 vapor, or by spraying with either phosphomolybdic acid (PMA) in aqueous ethanol, or after exposure to Cl$_2$, with a 4,4'-tetramethyldiaminodiphenylmethane reagent prepared according to E. Von Arx, M. Faupel and M Brugger, *J. Chromatography*, 1976, 220, 224-228.

Reversed phase high pressure liquid chromatography (RP-HPLC) was carried out using a Rainin HPLC employing a 41.4×300 mm, 8 uM, Dynamax™ C-18 column at a flow of 49 mL/min employing a gradient of acetonitrile:water (each containing 0.75% TFA) typically from 5 to 95% acetonitrile over 35-40 min. HPLC conditions are typically described in the format (5-95-35-214); this refers to a linear gradient of from 5% to 95% acetonitrile in water over 35 min while monitoring the effluent with a UV detector at a wavelength of 214 nM.

Methylene chloride (dichloromethane), 2-propanol, DMF, THF, toluene, hexane, ether, and methanol, were Fisher or Baker reagent grade and were used without additional purification except as noted, acetonitrile was Fisher or Baker HPLC grade and was used as is.

Definitions as used herein include:
DGAT is diacylglycerol:acyl CoA O-acyltransferase,
THF is tetrahydrofuran,
DMF is N,N-dimethylformamide,
DMA is N,N-dimethylacetamide,
DMSO is dimethylsulfoxide,
DCM is dichloromethane,
DME is dimethoxyethane,
MeOH is methanol,
EtOH is ethanol,
NaOH is sodium hydroxide,
TFA is 1,1,1-trifluoroacetatic acid,
HOBT is 1-hydroxybenzotriazole,
PyBroP is bromotripyrrolidinophosphonium hexafluorophosphate,
EDCI is 1-[3-(dimethylamino)propyl]-3-ethylcarbodiimide hydrochloride,
DIPEA is diisopropylethylamine,
brine is saturated aqueous sodium chloride solution,
DAG is 1,2-dioleoyl-sn-glycerol,
TLC is thin layer chromatography,
RP HPLC is reversed phase high performance liquid chromatography,
APCI-MS is atmospheric pressure chemical ionization mass spectrometry,
ES-MS is electrospray mass spectrometry,
RT is room or ambient temperature.

Silica gel chromatography on Biotage columns refers to use of a flash chromatography system supplied by the Biotage Division of the Dyax Corporation employing prepacked 40 g (40 s columns), 90 g (40 m columns) or 800 g (75 m columns). Elution is carried out with hexane-ethyl acetate mixtures under 10-15 psi nitrogen pressure.

Part I: Preferred Intermediates

Preparation of benzoic acid N'-isopropyl-hydrazide

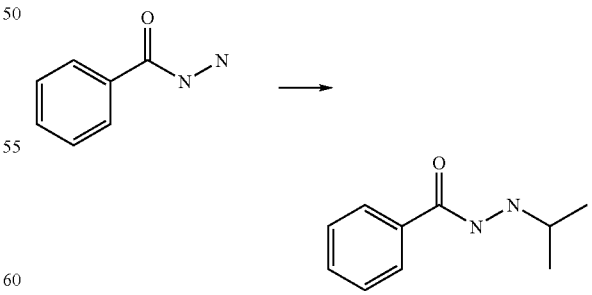

A solution of benzoylhydrazine (10 g, 73.45 mmol) in hexane (200 ml) was treated with acetone (54 mL, 734.5 mmol) and refluxed overnight. The precipitate was collected by suction filtration to afford a white solid which was treated with TFA (200 ml) and triethylsilane (24 mL, 149.24 mmol)

at 60° C. overnight. The reaction mixture was concentrated under reduced pressure. The residue was partitioned between DCM and 1N NaOH. The organic layer was washed with brine, dried over sodium sulfate, filtered, and concentrated to afford the product as a white solid (9.31 g, 71%).

Preparation of tetrahydro-pyran-4-carboxylic acid N'-isopropyl-hydrazide

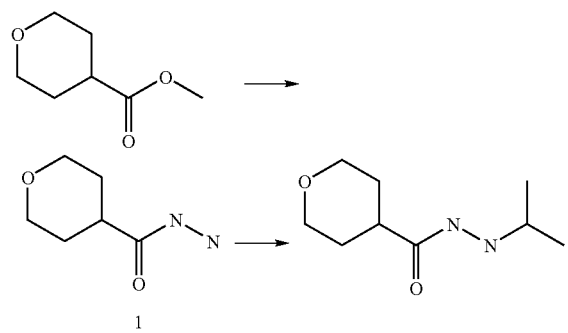

1

A solution of methyl tetrahydro-2H-pyran-4 (250 mg, 1.73 mmol) and hydrazine monohydrate (1.8 ml, 34.68 mmol) in MeOH (3 ml) was heated to 120° C. for 20 minutes in a microwave oven. The mixture was concentrated to dryness and the residue was triturated with hexanes. The resulting hydrazide 1 was collected by suction filtration and air dried (235 mg). This material was dissolved in acetone (3 ml) and heated to 60° C. for 20 min. The solution was concentrated to dryness. The residue was dissolved in TFA (10 ml) and treated with triethylsilane (0.65 ml, 4.10 mmol) at 60° C. overnight. The reaction mixture was concentrated under reduced pressure and the residue was partitioned between saturated sodium bicarbonate and ethyl acetate. The aqueous layer was saturated with brine and extracted with DCM. The combined organics were dried over sodium sulfate and concentrated under vacuum to afford the product as a white solid (198 mg, 53%).

Preparation of cyclohexane carboxylic acid N'-isopropyl-hydrazide

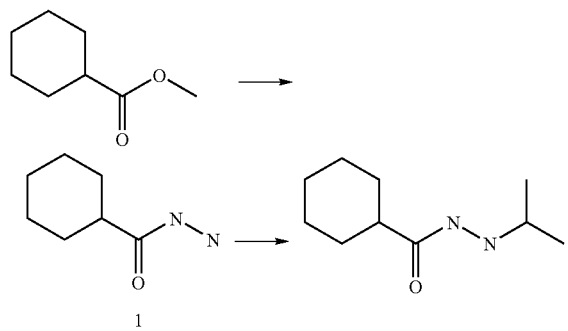

1

A solution of methyl-cyclohexane carboxylate (20 g, 140.65 mmol) and hydrazine monohydrate (35 ml, 703.25 mmol) in MeOH (100 ml) was refluxed overnight. The mixture was concentrated to dryness and the residue was partitioned between saturated aqueous sodium bicarbonate and DCM. The organic layer was washed with brine, dried over sodium sulfate, filtered and concentrated (14.35 g, 75%). A portion of the resulting hydrazide 1 (2.6 g, 18.28 mmol) was dissolved in acetone (100 ml) and the solution was refluxed overnight. The solution was concentrated to dryness. The residue was dissolved in TFA (30 ml) and treated with triethylsilane (5.83 ml, 36.56 mmol) at 60° C. overnight. The reaction mixture was concentrated under reduced pressure and the residue was partitioned between 1N NaOH and DCM. The organic layer was washed with brine, dried over sodium sulfate and concentrated under vacuum to afford the product as a white solid (2.0 g, 61%).

Preparation of thiophene-2-carboxylic acid N'-isopropyl-hydrazide

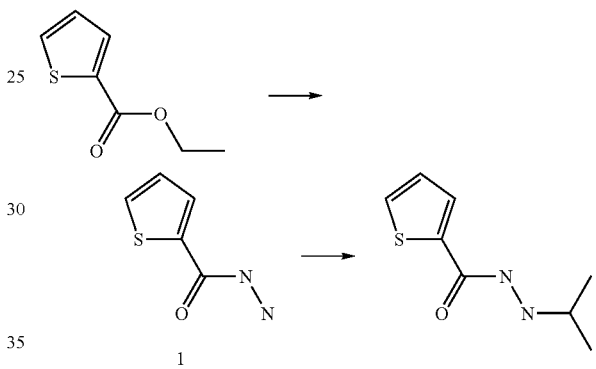

1

A solution of ethyl-2-thiophene carboxylate (2 g, 12.8 mmol) and hydrazine monohydrate (6.2 ml, 128 mmol) in EtOH (10 ml) was refluxed overnight. The mixture was concentrated to dryness to afford intermediate 1 as an off white solid (1.81 g). A portion of this material (500 mg) was dissolved in acetone (5 ml) and the solution was heated to 50° C. overnight. The solution was concentrated to dryness. The residue was dissolved in TFA (5 ml) and treated with triethylsilane (1.1 ml, 6.74 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (516 mg, 80%).

Preparation of furan-2-carboxylic acid N'-isopropyl-hydrazide

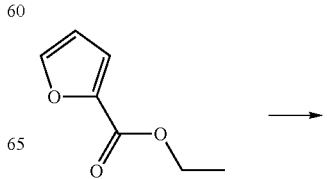

-continued

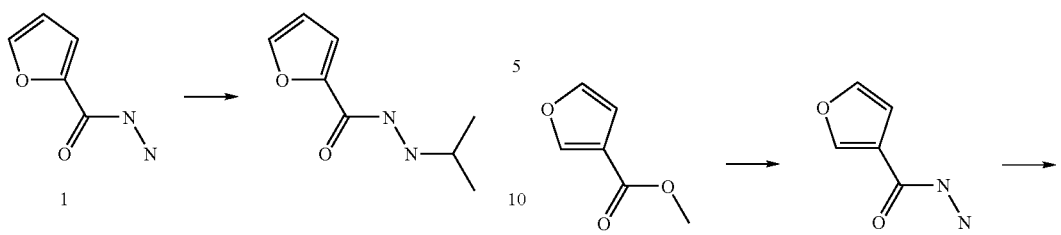

A solution of ethyl-2-furoate (2 g, 14.3 mmol) and hydrazine monohydrate (6.9 ml, 143 mmol) in EtOH (10 ml) was refluxed overnight. The mixture was concentrated to dryness to afford intermediate 1 (1.65 g). A portion of this material (500 mg) was dissolved in acetone (5 ml) and the solution was heated to 50° C. overnight. The solution was concentrated to dryness. The residue was dissolved in TFA (5 ml) and treated with triethylsilane (1.30 ml, 8.18 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (511 mg, 74%).

Preparation of thiophene-3-carboxylic acid
N'-isopropyl-hydrazide

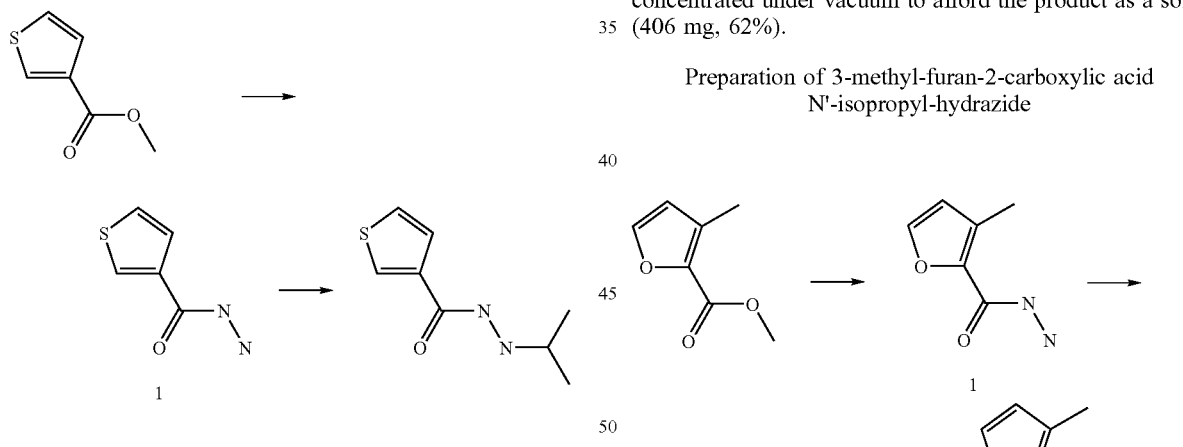

A solution of ethyl-3-thiophene carboxylate (2 g, 12.8 mmol) and hydrazine monohydrate (6.2 ml, 128 mmol) in EtOH (10 ml) was refluxed overnight. The mixture was concentrated to dryness to afford intermediate 1 (1.86 g, 100%). A portion of this material (500 mg) was dissolved in acetone (5 ml) and the solution was heated to 60° C. overnight. The solution was concentrated to dryness. The residue was dissolved in TFA (5 ml) and treated with triethylsilane (1.16 ml, 7.24 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a white solid (484 mg, 75%).

Preparation of furan-3-carboxylic acid
N'-isopropyl-hydrazide

A solution of ethyl-3-furoate (2 g, 14.3 mmol) and hydrazine monohydrate (6.9 ml, 143 mmol) in EtOH (10 ml) was refluxed overnight. The mixture was concentrated to dryness to afford intermediate 1 (1.52 g). A portion of this material (500 mg) was dissolved in acetone (5 ml) and the solution was heated to 60° C. overnight. The solution was concentrated to dryness. The residue was dissolved in TFA (5 ml) and treated with triethylsilane (1.25 ml, 7.82 mmol) at 60° C. overnight. The reaction mixture was concentrated under reduced pressure and the residue was partitioned between saturated aqueous bicarbonate and DCM. The organic layer was washed with brine, dried over sodium sulfate and concentrated under vacuum to afford the product as a solid (406 mg, 62%).

Preparation of 3-methyl-furan-2-carboxylic acid
N'-isopropyl-hydrazide

A solution of methyl-3-methyl-2-furoate (250 mg, 1.78 mmol) and hydrazine monohydrate (1.8 ml, 34.68 mmol) in MeOH (3 ml) was heated to 120° C. for 20 minutes in a microwave oven. The mixture was concentrated to dryness and the residue was triturated with hexanes. The resulting hydrazide 1 was collected by suction filtration and air dried (242 mg). This material was dissolved in acetone (3 ml) and stirred at rt overnight. The solution was concentrated to dryness. The residue was dissolved in TFA (3 ml) and treated with triethylsilane (0.58 ml, 3.6 mmol) at rt overnight. The reaction mixture was concentrated under reduced pressure and the residue was partitioned between saturated sodium bicarbonate and DCM. The organic layer was dried over sodium sulfate and concentrated under vacuum to afford the product as oil (268 mg, 82%).

Preparation of 4-(2-methoxy-ethoxy)-benzoic acid-N'-isopropyl hydrazide mmol) in MeOH (8 ml) was heated to 160° C. for 20 minutes in a microwave oven. The reaction mixture was concentrated under reduced pressure to afford hydrazide 2 as a yellow solid (790 mg, 79%). A solution of hydrazide 2 (200 mg, 0.95 mmol) in acetone (4 ml) was refluxed overnight. The reaction mixture was concentrated under reduced pressure to afford intermediate 3 as brown oil (240 mg, 100%). Compound 3 (240 mg, 0.95 mmol) was then treated with Et$_3$SiH

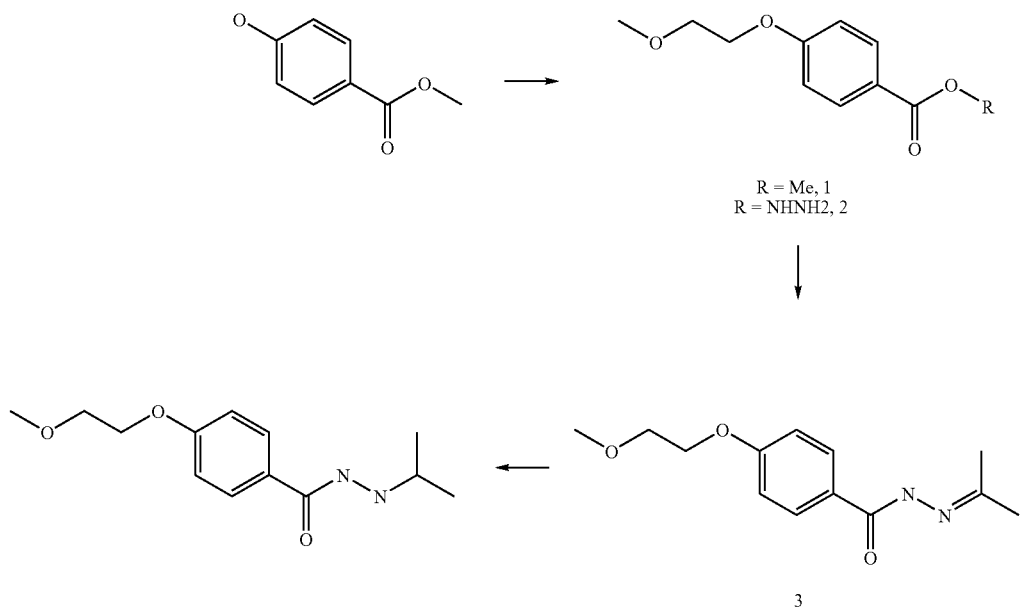

A DMF (20 ml) solution of methyl-p-hydroxybenzoate (1.0 g, 6.57 mmol), potassium carbonate (9.08 g, 65.72 mmol) and 2-bromoethyl methyl ether (6.17 ml, 65.72 mmol) was heated to 150° C. for 20 minutes in a microwave oven. The reaction mixture was filtered through celite, and partitioned between 1 N NaOH and ethyl acetate. The organic layer was washed with brine, dried over sodium sulfate, filtered and concentrated to afford intermediate 1 as pale yellow oil (1.28 g, 93%). A solution of ester 1 (1.0 g, 4.76 mmol) and hydrazine monohydrate (4.61 ml, 95.12

(0.35 ml, 2.1 mmol) in TFA (5 ml) at 60° C. overnight. The reaction mixture was concentrated and the residue was partitioned between DCM and 1N NaOH. The organic layer was washed with brine, dried over sodium sulfate, filtered and concentrated to afford the product as oil (170 mg, 62%).

Preparation of 2-(2-methoxy-ethoxy)-benzoic acid-N'-isopropyl hydrazide

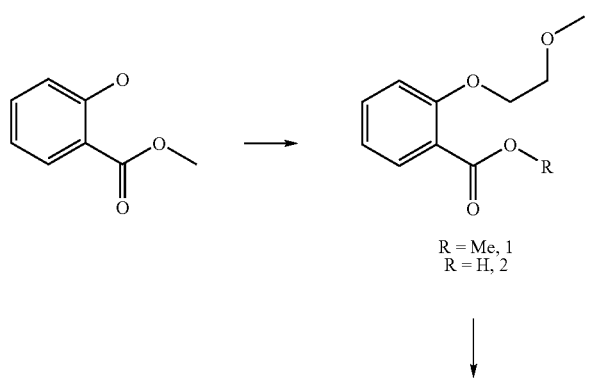

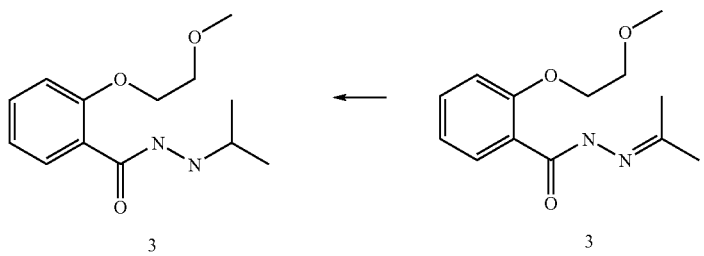

A DMF (20 ml) solution of methyl o-hydroxybenzoate (1.0 g, 6.57 mmol), potassium carbonate (9.08 g, 65.72 mmol) and 2-bromoethyl methyl ether (6.17 ml, 65.72 mmol) was heated to 150° C. for 20 minutes in a microwave oven. The reaction mixture was filtered through celite, and partitioned between 1 N NaOH and ethyl acetate. The organic layer was washed with brine, dried over sodium sulfate, filtered and concentrated to afford intermediate 1 as brown oil (807 mg, 58%). A solution of ester 1 (0.8 g, 3.8 mmol) and hydrazine monohydrate (4.0 ml, 76.0 mmol) in MeOH (8 ml) was heated to 160° C. for 20 minutes in a microwave oven. The reaction mixture was concentrated under reduced pressure to afford hydrazide 2 as oil (840 mg, 88%). A solution of hydrazide 2 (840 mg, 3.99 mmol) in acetone (10 ml) was refluxed overnight. The reaction mixture was concentrated under reduced pressure to afford intermediate 3 as brown oil (1.1 g, 100%). This crude material was then treated with Et$_3$SiH (1.5 ml, 9.25 mmol) in TFA (25 ml) at 60° C. overnight. The reaction mixture was concentrated and the residue was partitioned between DCM and 1N NaOH. The organic layer was washed with brine, dried over sodium sulfate, filtered and concentrated to afford the product as oil (460 mg, 40%).

Preparation of tetrahydro-thiopyran-4-carboxylic acid N'-isopropyl-hydrazide

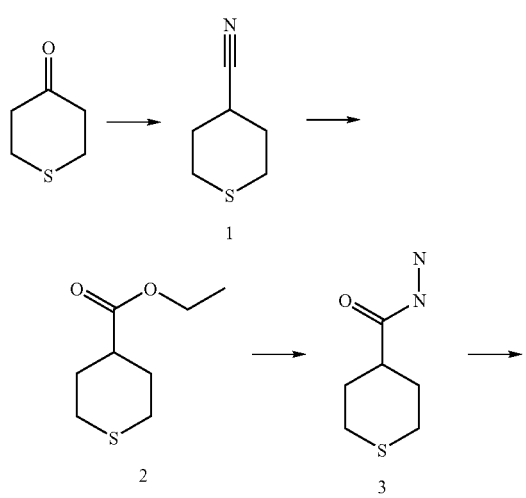

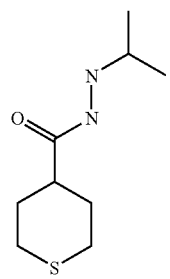

A cold (ice water bath) solution of tetrahydro-2H-thiopyran-4-one (3.57 g, 30.7 mmol) and tosylmethylisocyanide (6.61 g, 33.8 mmol) in DME (125 ml) was treated with a suspension of potassium t-butoxide (6.93 g, 61.8 mmoles) in t-butyl alcohol (100 ml). The reaction mixture was stirred at room temperature for 3 hours, and then diluted with ether (250 ml). The mixture was successively washed with water and brine, then dried over sodium sulfate, filtered, and concentrated. The crude product was purified by short path distillation under high vacuum to give nitrile 1 as colorless oil (1.98 g, 50.7%). A solution of nitrile 1 (1.0 g, 7.9 mmoles) in ethanol (15 ml) was cooled in an ice bath. Hydrogen chloride gas was bubbled into the solution until saturation. The reaction mixture was then stirred at room temperature for 2 hours. Water (5 ml) was added and stirring was continued at room temperature for 2.5 hours, at 60° C. for 4 hours, and finely at room temperature for 12 hours. The reaction mixture was concentrated and partitioned between water and ethyl acetate. The organic layer was successively washed with water and brine, then dried over sodium sulfate, filtered, and concentrated to afford ester 2 (539 mg, 40%). A solution of ester 2 (539 mg, 3.1 mmoles) and hydrazine monohydrate (3 ml, 61.9 mmoles) in MeOH (1 ml) was heated in a microwave oven at 160° C. for 10 min. Concentration of the reaction mixture under reduced pressure afforded hydrazide 3 (481 mg, 97%). A solution of 3 (481 mg, 3 mmoles) in acetone (2 ml) was heated in a microwave oven at 120° C. for 20 min. The acetone was removed under vacuum and the residue was dissolved in TFA (8 ml) and treated with triethylsilane (0.874 ml, 5.47 mmol) at 60° C., for 18 hours. The reaction mixture was concentrated and the residue was partitioned between saturated sodium bicarbonate solution and ethyl acetate. The organic layer was washed with brine, dried over sodium sulfate, filtered, and concentrated to afford the desired product (302 mg, 55%).

Preparation of 4-nitro-benzoic acid N'-isopropyl-hydrazide

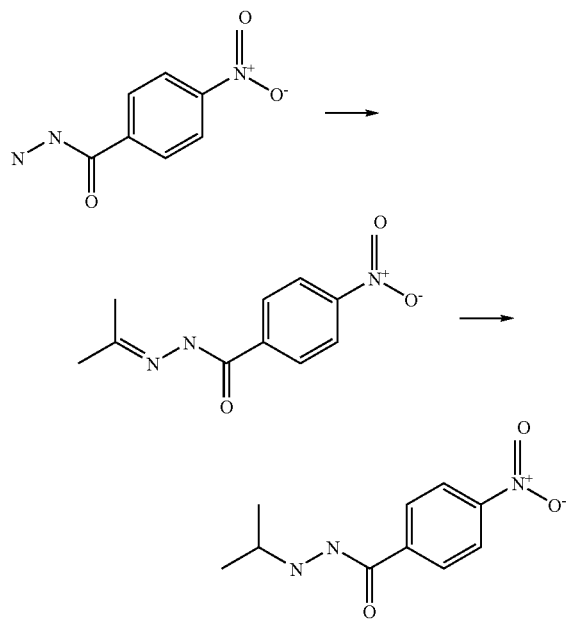

A solution of 4-nitrobenzoylhydrazine (2.5 g, 13.8 mmol) in hexane (50 ml) was treated with acetone (20.3 mL, 276 mmol) and refluxed overnight. The reaction mixture was cooled and the precipitate was collected by suction filtration, washed with hexanes and dried under vacuum to afford 2.9 g (13.12 mmol, 95%) of a white solid. This material was treated with TFA (19.5 ml) and triethylsilane (4.19 mL, 26.24 mmol) at 50-55° C. for 2 hours and then at RT overnight. The reaction mixture was diluted with 250 ml of 1N HCl and extracted with hexanes (2×100 ml). The aqueous layer was cooled in an ice bath and the pH was adjusted to 12.5 by the addition of NaOH pellets. This mixture was extracted with ethyl acetate (3×250 ml). The combined organic layers were dried over sodium sulfate, filtered, and concentrated. The residue was dissolved in 5% ethyl acetate/hexanes and poured through a silica gel plug. The silica gel was eluted with 35% ethyl acetate/hexanes and the filtrates were evaporated to afford the product as a white solid (3 g, 100%).

Preparation of (2-bromo-4-fluoro-phenoxy)-acetic acid-t-butyl ester

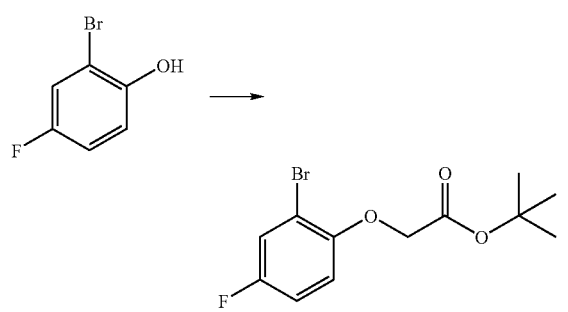

A solution of 2-bromo-4-fluorophenol (2.15 g, 11.25 mmol) in DMF (60 ml) was treated with potassium carbonate (7.77 g, 96.25 mmol) and t-butyl bromoacetate (1.99 ml, 13.5 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5%-10% ethyl acetate/hexanes gradient to give the product as colorless oil (2.86 g, 83%).

Preparation of (2'-ethyl-5-fluoro-biphenyl-2-yloxy)-acetic acid

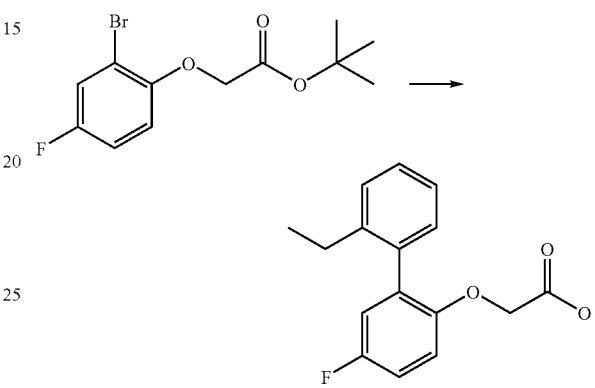

A solution of (2-bromo-4-fluoro-phenoxy)-acetic acid-t-butyl ester (2.00 g, 6.55 mmol) in DME (16 ml)/2M Na$_2$CO$_3$ (11.46 ml, 22.93 mmol) was treated with 2-ethylphenylboronic acid (1.96 g, 13.10 mmol), and Pd[PPh$_3$]$_4$ (757 mg, 0.655 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 5-20% ethyl acetate/hexanes gradient to afford 1.25 g of colorless oil (t-butyl ester). This material was dissolved in 4N HCl/dioxane (10 ml) and stirred at rt overnight. Concentration under reduced pressure afforded the product as colorless oil (1.08 g, 60%).

Preparation of (5-fluoro-2'-trifluoromethoxy-biphenyl-2-yloxy)-acetic acid

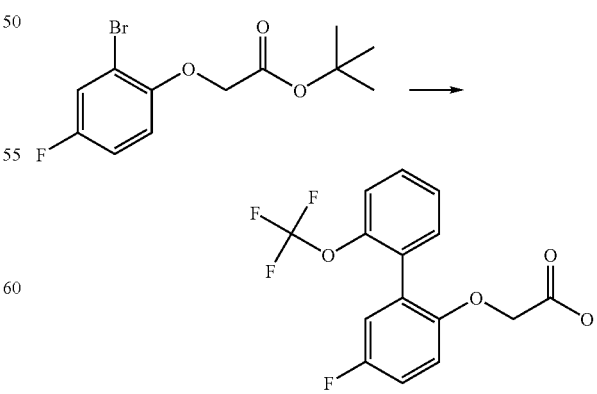

A solution of (2-bromo-4-fluoro-phenoxy)-acetic acid-t-butyl ester (5.1 g, 16.71 mmol) in DME (60 ml)/2M Na$_2$CO$_3$ (29.25 ml, 58.50 mmol) was treated with 2-trifluoromethoxyphenylboronic acid (5.16 g, 25.08 mmol), and Pd[PPh₃]₄ (3.87 g, 3.33 mmol) in a microwave oven at 150° C. for 15 min. The reaction mixture was partitioned between 1N HCl and ethyl acetate. The organic layer was successively washed with 1N NaOH and brine, then dried over sodium sulfate, filtered, and concentrated. The crude was absorbed on silica and purified on a silica gel column with a 8-10% ethyl acetate/hexanes gradient to afford 4.65 g of colorless oil (t-butyl ester). This material was dissolved in 4N HCl/dioxane (40 ml) and stirred at 60° C. for 2 h and then at rt overnight. Concentration under reduced pressure afforded the product as colorless oil (4.17 g, 24%).

Preparation of (2-bromo-4-fluoro-phenoxy)-acetic acid

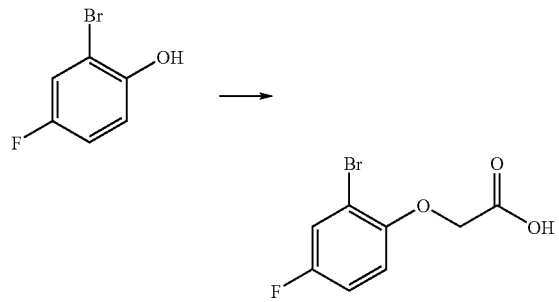

A solution of 2-bromo-4-fluorophenol (5.00 g, 26.18 mmol) in DMF (130 ml) was treated with potassium carbonate (18.45 g, 130.9 mmol) and t-butyl bromoacetate (4.64 ml, 31.41 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5%-10% ethyl acetate/hexanes gradient to afford the (t-butyl ester). This product was treated with 4 N HCl in dioxane (25 ml) at room temperature for 12 hours. The reaction mixture was concentrated, triturated with hexane, and filtered under suction to afford the product as a white solid (4.78 g, 74%).

Preparation of (2-bromo-phenylsulfanyl)-acetic acid

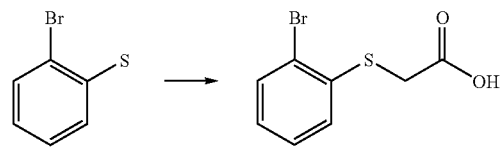

A solution of 2-bromo-benzenethiol (2.0 g, 10.6 mmol) in THF (20 ml) was treated with triethylamine (3.54 ml, 25.4 mmol) and t-butyl bromoacetate (1.64 ml, 11.1 mmol) at rt for 2 hours. The reaction mixture was filtered through celite, and partitioned between water and ethyl acetate. The organic layer was washed with brine, dried over sodium sulfate, filtered and concentrated to afford the t-butyl ester. This material was treated with 4 N HCl in dioxane (20 ml) at room temperature for 18 hours. The reaction mixture was concentrated and the residue was partitioned between water and ethyl acetate. The organic layer was washed with brine, dried over sodium sulfate, filtered and concentrated under vacuum to afford the product as a white solid (2.65 g, 100%).

Preparation of (2-cyclopentyl-phenoxy)-acetic acid

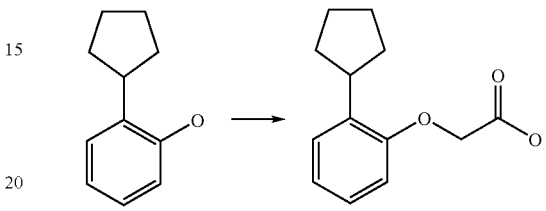

A mixture of 2-cyclopentylphenol (1.00 g, 6.164 mmol) and t-butyl bromoacetate (1.09 ml, 7.39 mmol) in DMF (30 ml) was treated with potassium carbonate (4.25 g, 30.82 mmol) and stirred at 60° C. for 5 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 10-20% ethyl acetate/hexanes gradient to afford the t-butyl ester as a white solid. This material was treated with 4 N HCl in dioxane (10 ml) at room temperature for 72 hours. The reaction mixture was concentrated, and the solid residue was triturated with hexane, and then collected by filtration (1.26 g, 93%).

Preparation of (2-sec-butyl-phenoxy)-acetic acid

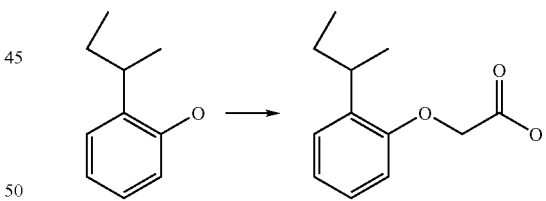

A mixture of 2-sec-butyl-phenol (1.00 g, 6.66 mmol) and t-butyl bromoacetate (1.18 ml, 7.98 mmol) in DMF (35 ml) was treated with potassium carbonate (4.60 g, 33.28 mmol) and stirred at 60° C. for 5 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 10-20% ethyl acetate/hexanes gradient to afford the t-butyl ester as a white solid. This material was treated with 4 N HCl in dioxane (25 ml) at room temperature for 12 hours. The reaction mixture was concentrated, and the solid residue was triturated with hexane, and then collected by filtration (1.46 g, 100%).

Preparation of (2-propyl-phenoxy)-acetic acid

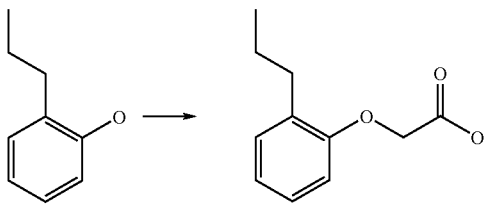

A mixture of 2-propyl-phenol (1.00 g, 9.89 mmol) and t-butyl bromoacetate (1.5 ml, 10.1 mmol) in DMF (35 ml) was treated with potassium carbonate (5.07 g, 36.7 mmol) and stirred at 60° C. for 5 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 10-20% ethyl acetate/hexanes gradient to afford the t-butyl ester as a white solid. This material was treated with 4 N HCl in dioxane (25 ml) at room temperature for 72 hours. The reaction mixture was concentrated, and the solid residue was triturated with hexane, and then collected by filtration (1.63 g, 85%).

Preparation of (2-benzyl-phenoxy)-acetic acid

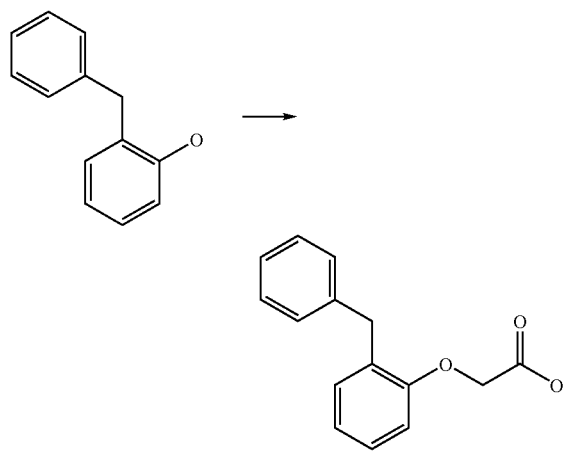

A mixture of 2-benzyl-phenol (1.00 g, 5.43 mmol) and t-butyl bromoacetate (0.962 ml, 6.52 mmol) in DMF (30 ml) was treated with potassium carbonate (3.75 g, 27.15 mmol) and stirred at 60° C. for 5 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5-10% ethyl acetate/hexanes gradient to afford the t-butyl ester as a white solid. This material was treated with 4 N HCl in dioxane (25 ml) at room temperature for 12 hours. The reaction mixture was concentrated, and the solid residue was triturated with hexane, and then collected by filtration (1.15 g, 97%).

Preparation of benzoic acid N'-[2-(2-bromo-4-fluoro-phenoxy)-acetyl]-N'-isopropyl-hydrazide

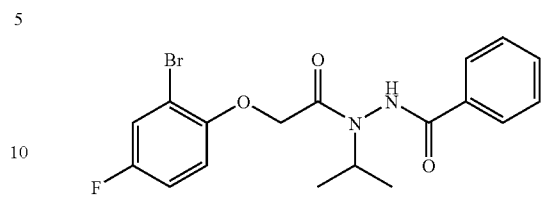

A solution of (2-bromo-4-fluoro-phenoxy)-acetic acid (2.00 g, 8.03 mmol) and benzoic acid N'-isopropyl-hydrazide (1.72 g, 9.63 mmol) in DMF (20 mL) was treated with diisopropylethyl amine (3.5 mL, 20.07 mmol) and bromotripyrrolidinophosphonium hexafluorophosphate (PyBroP, 5.62 g, 12.04 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 20-30% ethyl acetate/hexanes gradient to afford the product as a white crystalline solid (2.29 g, 70%).

Preparation of benzoic acid N'-[2-(2-bromo-phenylsulfanyl)-acetyl]-N'-isopropyl-hydrazide

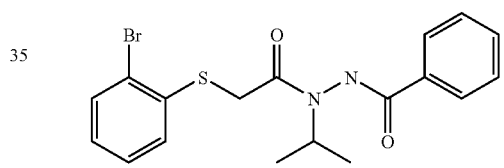

A solution of (2-bromo-phenylsulfanyl)-acetic acid (694 mg, 2.81 mmol) and benzoic acid N'-isopropyl-hydrazide (500 mg, 2.81 mmol) in DMF (10 mL) was treated with triethylamine (1.17 ml, 8.43 mmol), HOBT (455 mg, 3.37 mmol) and EDCI (645 mg, 3.37 mmol) at room temperature overnight. The reaction mixture was partitioned between water and ethyl acetate. The organic layer was successively washed with 1N HCl, aqueous saturated sodium bicarbonate, and brine, then dried over sodium sulfate, filtered and concentrated. Pure product was obtained by crystallization from ethyl acetate (611 mg, 54%).

Preparation of cyclohexanecarboxylic acid N'-[2-(2-bromo-4-fluoro-phenoxy)-acetyl]-N'-isopropyl-hydrazide

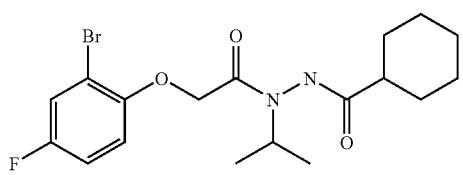

A solution of (2-bromo-4-fluoro-phenoxy)-acetic acid (249 mg, 1.0 mmol) and cyclohexane carboxylic acid N'-isopropyl-hydrazide (221 mg, 1.2 mmol) in DMF (10 ml) was treated with diisopropylethyl amine (0.44 mL, 2.5 mmol) and bromotripyrrolidinophosphonium hexafluorophosphate (PyBroP, 700 mg, 1.5 mmol) at room temperature overnight. The reaction mixture was partitioned between 1N HCl and ethyl acetate. The organic layer was successively washed with saturated 1N NaOH and brine, then dried over sodium sulfate, filtered and concentrated. The crude was absorbed on silica and purified on a silica gel column with a 30-50% ethyl acetate/hexanes gradient to afford the product as a white solid (310 mg, 75%).

Preparation of 4-(2-methoxy-ethoxy)-benzoic acid N'-[2-(2-bromo-4-fluoro-phenoxy)-acetyl]-N'-isopropyl-hydrazide

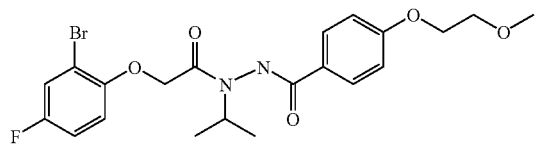

A solution of (2-bromo-4-fluoro-phenoxy)-acetic acid (164 mg, 0.66 mmol) and 4-(2-methoxy-ethoxy)-benzoic acid-N'-isopropyl hydrazide (200 mg, 0.79 mmol) in DMF (5 ml) was treated with diisopropylethyl amine (0.29 mL, 1.65 mmol) and PyBroP (462 mg, 0.99 mmol) at room temperature overnight. The reaction mixture was partitioned between 1N HCl and ethyl acetate. The organic layer was successively washed with water and brine, then dried over sodium sulfate, filtered and concentrated. The crude was absorbed on silica and purified on a silica gel column with a 45-60% ethyl acetate/hexanes gradient to afford the product as a solid (202 mg, 63%).

Preparation of thiophene-2-carboxylic acid N'-[2(2-bromo-4-fluoro-phenoxy)-acetyl]-N'-isopropyl-hydrazide

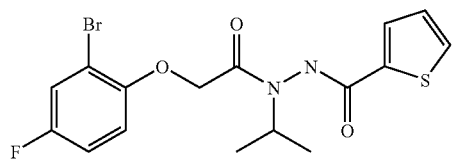

A solution of (2-bromo-4-fluoro-phenoxy)-acetic acid (220 mg, 0.91 mmol) and thiophene-2-carboxylic acid N'-isopropyl-hydrazide (200 mg, 1.09 mmol) in DMF (5 ml) was treated with diisopropylethyl amine (0.40 mL, 2.28 mmol) and PyBroP (636 mg, 1.37 mmol) at room temperature overnight. The reaction mixture was partitioned between 1N HCl and ethyl acetate. The organic layer was washed with brine, then dried over sodium sulfate, filtered and concentrated. The crude was absorbed on silica and purified on a silica gel column with a 10-50% ethyl acetate/hexanes gradient to afford the product as a solid (263 mg, 70%).

Preparation of thiophene-3-carboxylic acid N'-[2-(2-bromo-4-fluoro-phenoxy)-acetyl]-N'-isopropyl-hydrazide

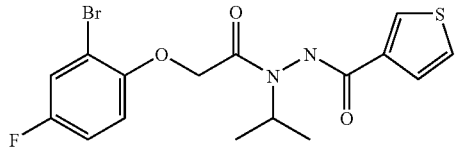

A solution of (2-bromo-4-fluoro-phenoxy)-acetic acid (226 mg, 0.91 mmol) and thiophene-3-carboxylic acid N'-isopropyl-hydrazide (200 mg, 1.09 mmol) in DMF (5 ml) was treated with diisopropylethyl amine (0.40 mL, 2.28 mmol) and PyBroP (636 mg, 1.37 mmol) at room temperature overnight. The reaction mixture was partitioned between 1N HCl and ethyl acetate. The organic layer was washed with brine, then dried over sodium sulfate, filtered and concentrated. The crude was absorbed on silica and purified on a silica gel column with a 30-50% ethyl acetate/hexanes gradient to afford the product as a solid (251 mg, 66%).

Preparation of tetrahydro-thiopyran-4-carboxylic acid N'-[2-(2-bromo-4-fluoro-phenoxy)-acetyl]-N'-isopropyl-hydrazide

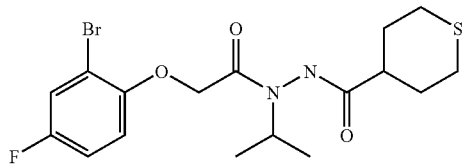

A solution of tetrahydro-thiopyran-4-carboxylic acid N'-isopropyl-hydrazide (300 mg, 1.48 mmol) and (2-bromo-4-fluoro-phenoxy)-acetic acid (369 mg, 1.48 mmol) in DMF (6 ml) was treated at rt with HOBT (240 mg, 1.78 mmol), EDCI (341 mg, 1.78 mmol), and triethylamine (0.620 ml, 4.45 mmol). The reaction mixture was stirred at room temperature for 18 hours and then partitioned between 1N HCl solution and ethyl acetate. The organic layer was washed with water, brine, dried over sodium sulfate, filtered and concentrated under vacuum. The crude was purified by RP HPLC to afford the product as a solid (116 mg, 18.1%).

Preparation of (2-bromo-4-methyl-phenoxy)-acetic acid

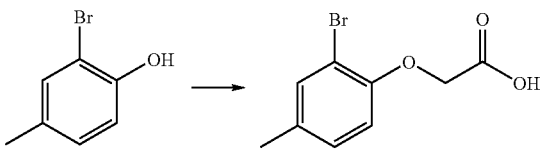

A solution of 3-bromo-4-methylphenol (1.00 g, 5.35 mmol) in DMF (25 mL) was treated with potassium carbonate (3.69 g, 23.9 mmol) and t-butyl bromoacetate (0.95 ml, 5.74 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5-10% ethyl acetate/hexanes gradient to give a white solid (t-butyl-ester). This product was treated with 4 N HCl in dioxane (10 ml) at room temperature for 12 hours. The reaction mixture was concentrated, triturated with hexane, and filtered under suction to afford the product as a white solid (0.88 g, 3.34 mmol, 63%).

Preparation of benzoic acid N'-[2-(2-bromo-4-methyl-phenoxy)-acetyl]-N'-isopropyl-hydrazide

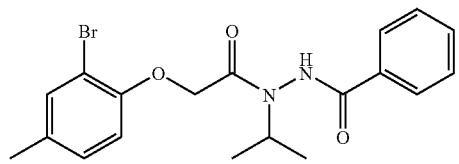

A solution of (2-bromo-4-methyl-phenoxy)-acetic acid (879 mg, 3.34 mmol) and benzoic acid N'-isopropyl-hydrazide (714 mg, 4.00 mmol) in DMF (20 mL) was treated with diisopropylethyl amine (1.45 ml, 8.35 mmol) and PyBroP (2.33 g, 5.01 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 20-30% ethyl acetate/hexanes gradient to afford the product as a white solid (463 mg, 34%).

Preparation of (2-bromo-4,5-difluoro-phenoxy)-acetic acid

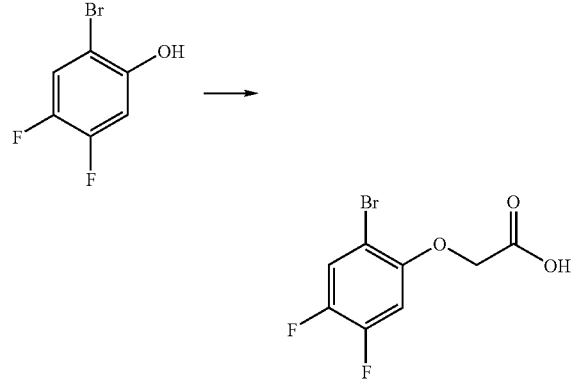

A solution of 2-bromo-4,5-difluorophenol (1.00 g, 4.78 mmol) in DMF (25 mL) was treated with potassium carbonate (3.3 g, 23.9 mmol) and t-butyl bromoacetate (0.85 ml, 5.736 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5-10% ethyl acetate/hexanes gradient to give a white solid (t-butyl-ester). This product was treated with 4 N HCl in dioxane (10 ml) at room temperature for 12 hours. The reaction mixture was concentrated, triturated with hexane, and filtered under suction to afford the product as a white solid (985, 72%).

Preparation of benzoic acid N'-[2-(2-bromo-4,5-difluoro-phenoxy)-acetyl]-N'-isopropyl-hydrazide

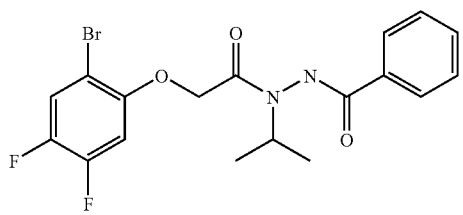

A solution of (2-bromo-4,5-difluoro-phenoxy)-acetic acid (985 mg, 3.68 mmol) and benzoic acid N'-isopropyl-hydrazide (787 mg, 4.416 mmol) in DMF (20 mL) was treated with diisopropylethyl amine (1.6 mL, 9.2 mmol) and PyBroP (2.57 g, 5.52 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 20-30% ethyl acetate/hexanes gradient to afford the product as a white solid (832 mg, 34%).

Preparation of (2-bromo-4,6-difluoro-phenoxy)-acetic acid

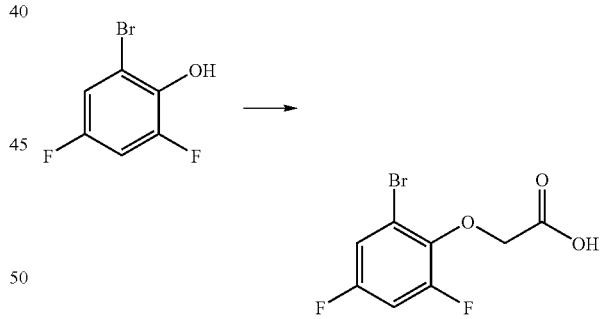

A solution of 2-bromo-4,6-difluorophenol (1.00 g, 4.78 mmol) in DMF (25 ml) was treated with potassium carbonate (3.3 g, 23.9 mmol) and t-butyl bromoacetate (0.85 ml, 5.74 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5-10% ethyl acetate/hexane gradient to afford a white solid (t-butyl ester). This product was treated with 4 N HCl in dioxane (10 ml) at room temperature for 12 hours. The reaction mixture was concentrated, triturated with hexane, and filtered under suction to afford a white solid (0.92 g, 72%).

Preparation of benzoic acid N'-[2-(2-bromo-4,6-difluoro-phenoxy)-acetyl]-N'-isopropyl-hydrazide

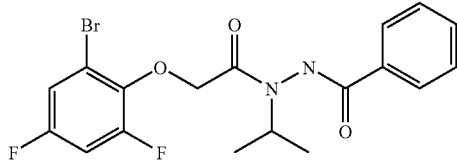

A solution of (2-bromo-4,6-difluoro-phenoxy)-acetic acid (0.92 g, 3.45 mmol) and benzoic acid N'-isopropyl-hydrazide (738 mg, 4.14 mmol) in DMF (20 ml) was treated with diisopropylethyl amine (1.5 ml, 8.625 mmol) and PyBroP (2.41 g, 5.175 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 20-30% ethyl acetate/hexanes gradient to afford the product as a white solid (478 mg, 1.12 mmol, 32%).

Preparation of (2-bromo-4-cyano-phenoxy)-acetic acid

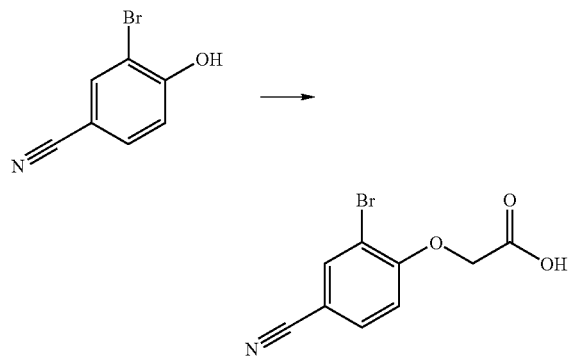

A solution of 3-bromo-4-hydyroxybenzonitrile (1.00 g, 5.05 mmol) in DMF (25 ml) was treated with potassium carbonate (3.48 g, 25.25 mmol) and t-butyl bromoacetate (0.895 ml, 6.06 mmol) at 60° C. for 12 hours. The reaction mixture was filtered through celite, and partitioned between water and ethyl acetate. The organic layer was washed with brine, dried over sodium sulfate, filtered and concentrated. The crude was absorbed on silica and purified on a silica gel column with a 5-10% ethyl acetate/hexanes gradient to a white solid (t-butyl ester). The product was treated with 4 N HCl in dioxane (25 ml) at room temperature for 12 hours. The reaction mixture was concentrated, triturated with hexane, and filtered under suction to afford a white solid (1.1 g, 70%).

Preparation of benzoic acid N'-[2-(2-bromo-4-cyano-phenoxy)-acetyl]-N'-isopropyl-hydrazide

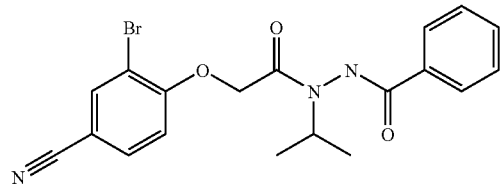

A solution of (2-bromo-4-cyano-phenoxy)-acetic acid (910 mg, 3.5 mmol) and benzoic acid N'-isopropyl-hydrazide (749 mg, 4.2 mmol) in DMF (20 ml) was treated with diisopropylethyl amine (1.52 mL, 8.75 mmol) and PyBroP (2.45 g, 5.25 mmol) at room temperature overnight. The reaction mixture was partitioned between 1N HCl and ethyl acetate. The organic layer was washed with saturated sodium bicarbonate, brine, dried over sodium sulfate, filtered and concentrated. The crude was absorbed on silica and purified on a silica gel column with a 20-30% ethyl acetate/hexanes gradient to afford the product as a white solid (410 mg, 0.9849 mmol, 28%).

Part II: Preparation of Preferred Compounds

Example 1

Preparation of benzoic acid N'-[2-(5,4'-difluoro-biphenyl-2-yloxy)-acetyl]-N'-isopropyl-hydrazide

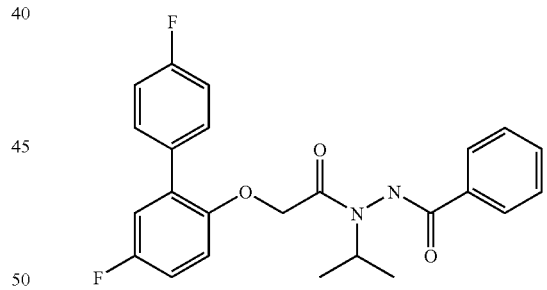

A solution of benzoic acid N'-[2-(2-bromo-4-fluoro-phenoxy)-acetyl]-N'-isopropyl-hydrazide (50 mg, 0.122 mmol) in DME (3 ml)/2M Na$_2$CO$_3$ (215 uL, 0.427 mmol) was treated with 4-fluorobenzeneboronic acid (26 mg, 0.183 mmol) and Pd[PPh$_3$]$_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a beige solid (42 mg, 81%). LC-MS m/e 425.28 (M+H$^+$)

Example 2

Preparation of benzoic acid N'-[2-(2'-chloro-5-fluoro-biphenyl-2-yloxy)-acetyl]-N'-isopropyl-hydrazide

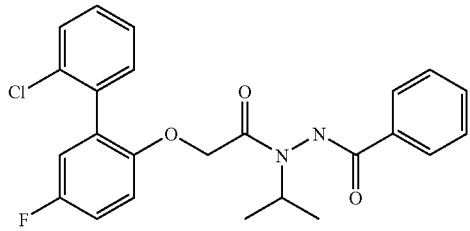

A solution of benzoic acid N'-[2-(2-bromo-4-fluoro-phenoxy)-acetyl]-N'-isopropyl-hydrazide (60 mg, 0.147 mmol) in DME (3 ml)/2M $Na_2CO_3$ (256 uL, 0.513 mmol) was treated with 3-chlorophenylboronic acid (34 mg, 0.219 mmol) and $Pd[PPh_3]_4$ (34 mg, 0.029 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a white crystalline solid (52 mg, 80%). LC-MS m/e 441.24 (M+H$^+$)

Example 3

Preparation of benzoic acid N'-[2-(5-fluoro-2'-methyl-biphenyl-2-yloxy)-acetyl]-N'-isopropyl-hydrazide

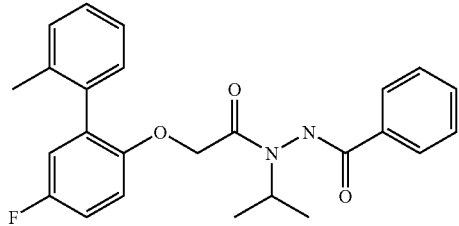

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-tolylboronic acid (25 mg, 0.183 mmol) and $Pd[PPh_3]_4$ (28 mg, 0.024 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a beige solid (23 mg, 44%). LC-MS m/e 421.31 (M+H$^+$)

Example 4

Preparation of benzoic acid N'-[2-(5-fluoro-2'-methoxy-biphenyl-2-yloxy)-acetyl]-N'-isopropyl-hydrazide

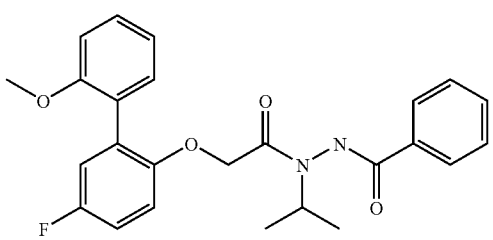

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-methoxyphenylboronic acid (28 mg, 0.183 mmol) and $Pd[PPh_3]_4$ (28 mg, 0.024 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a beige solid (39 mg, 73%). LC-MS m/e 437.29 (M+H$^+$)

Example 5

Preparation of benzoic acid N'-[2-(5,2'-difluoro-biphenyl-2-yloxy)-acetyl]-N'-isopropyl-hydrazide

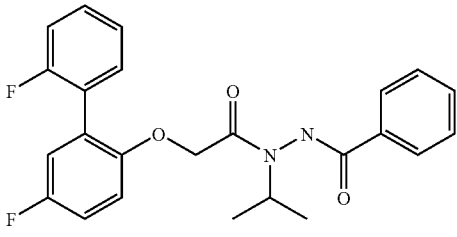

A solution of benzoic acid N'-[2-(2-bromo-4-fluoro-phenoxy)-acetyl]-N'-isopropyl-hydrazide (50 mg, 0.122 mmol) in DME (3 mL)/2M $Na_2CO_3$ (0.215 ml, 0.427 mmol) was treated with 2-fluorophenylboronic acid (26 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a beige solid (30 mg, 58%). LC-MS m/e 425.28 (M+H$^+$)

Example 6

Preparation of benzoic acid N'-[2-(5-fluoro-4'-methoxy-biphenyl-2-yloxy)-acetyl]-N'-isopropyl-hydrazide

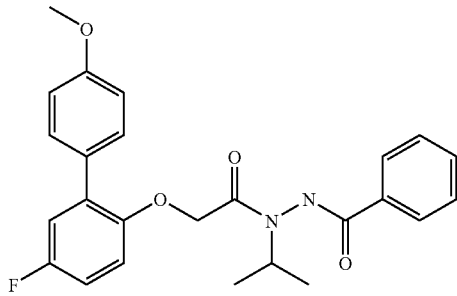

A solution of benzoic acid N'-[2-(2-bromo-4-fluoro-phenoxy)-acetyl]-N'-isopropyl-hydrazide (50 mg, 0.122 mmol) in DME (3 mL)/2M $Na_2CO_3$ (0.215 ml, 0.427 mmol) was treated 4-methoxyphenylboronic acid (28 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a beige solid (47 mg, 88%). LC-MS m/e 437.31 (M+H$^+$)

Example 7

Preparation of benzoic acid N'-[2-(4'-chloro-5-fluoro-biphenyl-2-yloxy)-acetyl]-N'-isopropyl-hydrazide

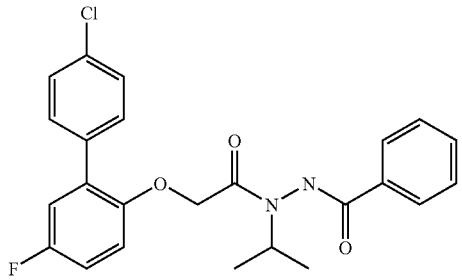

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 4-chlorophenylboronic acid (29 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a beige solid (15 mg, 0.034 mmol, 27%). LC-MS m/e 441.25 (M+H$^+$)

Example 8

Preparation of benzoic acid N'-[2-(5-fluoro-3'-methoxy-biphenyl-2-yloxy)-acetyl]-N'-isopropyl-hydrazide

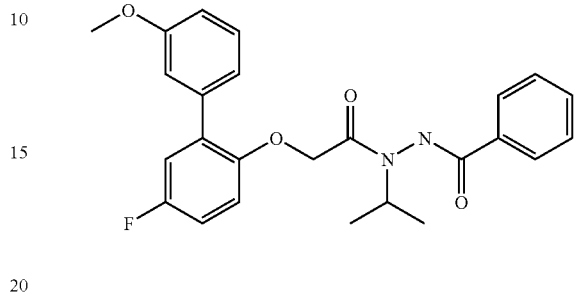

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 3-methoxyphenylboronic acid (28 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a beige solid (44 mg, 83%). MS m/e 437.29 (M+H$^+$)

Example 9

Preparation of benzoic acid N'-[2-(5,3'-difluoro-biphenyl-2-yloxy)-acetyl]-N'-isopropyl-hydrazide

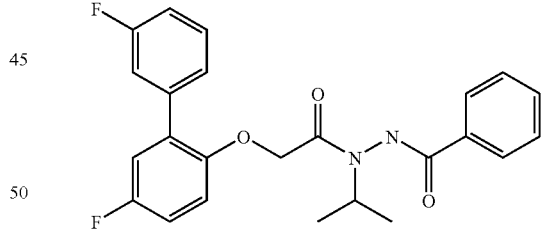

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 3-fluorobenezeneboronic acid (26 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a white solid (35 mg, 68%). LC-MS m/e 425.28 (M+H$^+$)

Example 10

Preparation of benzoic acid N'-[2-(5,3'-difluoro-biphenyl-2-yloxy)-acetyl]-N'-isopropyl-hydrazide

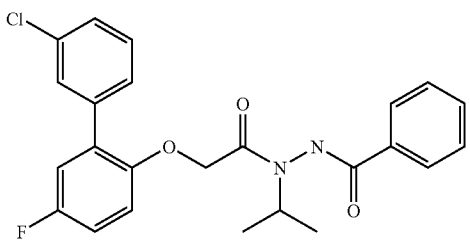

A solution of benzoic acid N'-[2-(2-bromo-4-fluoro-phenoxy)-acetyl]-N'-isopropyl-hydrazide (50 mg, 0.122 mmol) in DME (3 ml)/2M Na$_2$CO$_3$ (0.215 ml, 0.427 mmol) was treated with 3-chlorobenezeneboronic acid (29 mg, 0.183 mmol) and Pd[PPh$_3$]$_4$ (28 mg, 0.0244 mmol) at 90° C. overnight. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a white solid (45 mg, 84%). LC-MS m/e 441.24 (M+H$^+$)

Example 11

Preparation of benzoic acid N'-[2-(5-fluoro-biphenyl-2-yloxy)-acetyl]-N'-isopropyl-hydrazide

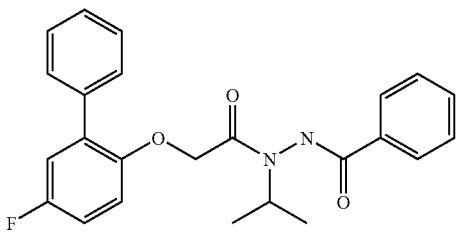

A solution of benzoic acid N'-[2-(2-bromo-4-fluoro-phenoxy)-acetyl]-N'-isopropyl-hydrazide (50 mg, 0.122 mmol) in DME (3 ml)/2M Na$_2$CO$_3$ (0.215 ml, 0.427 mmol) was treated with phenylboronic acid (22 mg, 0.183 mmol) and Pd[PPh$_3$]$_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a white solid (44 mg, 89%). MS m/e 407.22 (M+H$^+$)

Example 12

Preparation of benzoic acid N'-[2-(5-fluoro-3'-isopropyl-biphenyl-2-yloxy)-acetyl]-N'-isopropyl-hydrazide

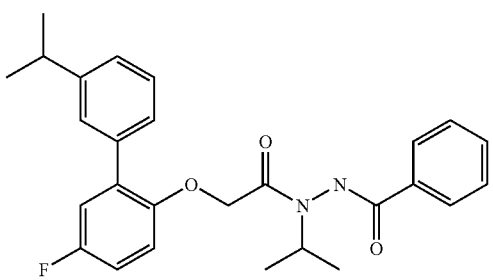

A solution of benzoic acid N'-[2-(2-bromo-4-fluoro-phenoxy)-acetyl]-N'-isopropyl-hydrazide (50 mg, 0.122 mmol) in DME (3 ml)/2M Na$_2$CO$_3$ (0.215 ml, 0.427 mmol) was treated with 3-isopropylbenzylboronic acid (30 mg, 0.183 mmol) and Pd[PPh$_3$]$_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a white solid. (34 mg, 62%). MS m/e 449.30 (M+H$^+$)

Example 13

Preparation of benzoic acid N'-[2-(5-fluoro-2'-methylsylfanyl-biphenyl-2-yloxy)-acetyl]-N'-isopropyl-hydrazide

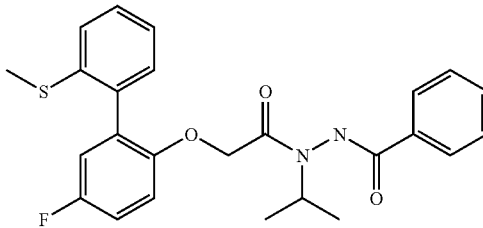

A solution of benzoic acid N'-[2-(2-bromo-4-fluoro-phenoxy)-acetyl]-N'-isopropyl-hydrazide (50 mg, 0.122 mmol) in DME (3 ml)/2M Na$_2$CO$_3$ (0.215 ml, 0.427 mmol) was treated with 2-methylthiophenylboronic acid (31 mg, 0.183 mmol) and Pd[PPh$_3$]$_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a white solid (36 mg, 0.0795 mmol, 65%). MS m/e 453.19 (M+H$^+$)

Example 14

Preparation of benzoic acid N'-[2-(5-fluoro-2'-nitro-biphenyl-2-yloxy)-acetyl]-N'-isopropyl-hydrazide

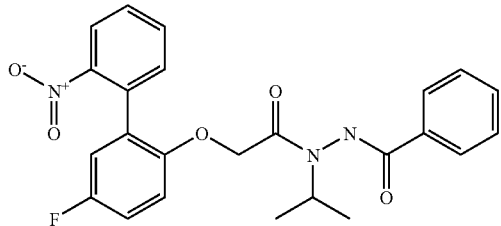

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-nitrophenylboronic acid (31 mg, 0.183 mmol) and Pd[PPh$_3$]$_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was purified first on a silica gel column with 30% ethyl acetate/hexanes and then by RP HPLC to afford the product as a white solid (12 mg, 21%). MS m/e 452.18 (M+H$^+$)

Example 15

Preparation of benzoic acid N'-[2-(5-fluoro-2'-isopropoxy-biphenyl-2-yloxy)-acetyl]-N'-isopropyl-hydrazide

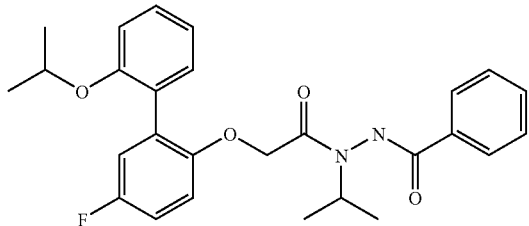

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-isopropoxylphenylboronic acid (32 mg, 0.183 mmol) and Pd[PPh$_3$]$_4$ (27 mg, 0.0244 mmol) for 12 hours at 90° C. The reaction mixture was partitioned between water and ethyl acetate. The organic layer was washed with brine, dried over sodium sulfate, filtered, and concentrated. The crude was purified first on a silica gel column with 30% ethyl acetate/hexanes then by RP HPLC to afford the product as a white solid (22 mg, 38%). MS m/e 465.27 (M+H$^+$)

Example 16

Preparation of benzoic acid N'-[2-(2'-ethyl-5-fluoro-biphenyl-2-yloxy)-acetyl]-N'-isopropyl-hydrazide

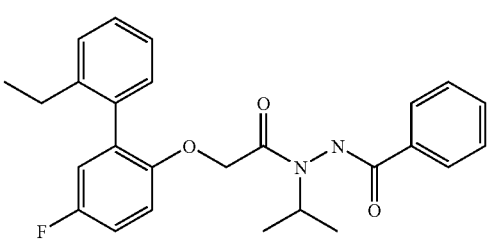

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-ethylphenylboronic acid (27 mg, 0.183 mmol) and Pd[PPh$_3$]$_4$ (27 mg, 0.024 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 20-30% ethyl acetate/hexanes gradient to afford the product (19 mg, 36%). MS m/e 435.44 (M+H$^+$)

Example 17

Preparation of benzoic acid N'-[2-(5-fluoro-2'-propoxy-biphenyl-2-yloxy)-acetyl]-N'-isopropyl-hydrazide

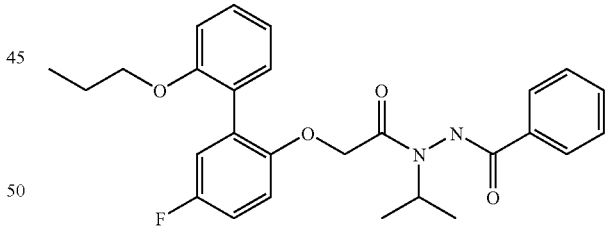

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-propoxyphenylboronic acid (33 mg, 0.183 mmol) and Pd[PPh$_3$]$_4$ (27 mg, 0.0244 mmol) for 12 hours at 90° C. The reaction mixture was partitioned between water and ethyl acetate. The organic layer was washed with brine, dried over sodium sulfate, filtered, and concentrated. The crude was purified first on a silica gel column with a 20-30% ethyl acetate/hexanes gradient and then by RP HPLC to afford the product as a white solid (42 mg, 74%). MS m/e 407.23 (M+H$^+$)

Example 18

Preparation of benzoic acid N'-[2-(2'-methoxycarbonyl-5-fluoro-biphenyl-2-yloxy)-acetyl]-N'-isopropyl-hydrazide

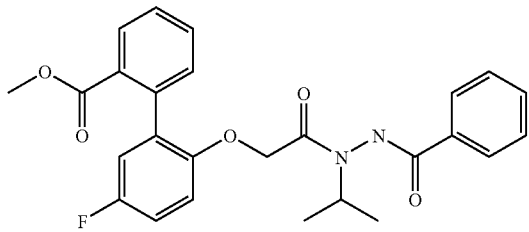

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-methoxycarbonylphenyl boronic acid (33 mg, 0.183 mmol) and $Pd[PPh_3]_4$ (27 mg, 0.0244 mmol) for 12 hours at 90° C. The reaction mixture was partitioned between water and ethyl acetate. The organic layer was washed with brine, dried over sodium sulfate, filtered, and concentrated. The crude was purified first on a silica gel column with a 20-30% ethyl acetate/hexanes gradient and then by RP HPLC to afford the product as a white solid (8 mg, 14%). MS m/e 465.23 $(M+H^+)$

Example 19

Preparation of benzoic acid N'-[2-(2',3'-dimethyl-5-fluoro-biphenyl-2-yloxy)-acetyl]-N'-isopropyl-hydrazide

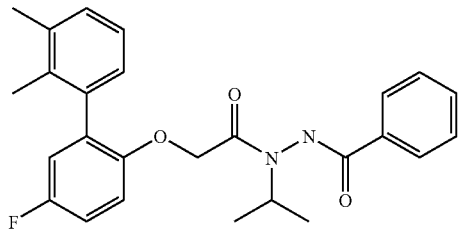

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2,3-dimethylphenylboronic acid (27 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 20-30% ethyl acetate/hexanes gradient to afford the product as a white solid (30 mg, 57%). MS m/e 435.30 $(M+H^+)$

Example 20

Preparation of benzoic acid N'-[2-(5-fluoro-2'-trifluoromethoxy-biphenyl-2-yloxy)-acetyl]-N'-isopropyl-hydrazide

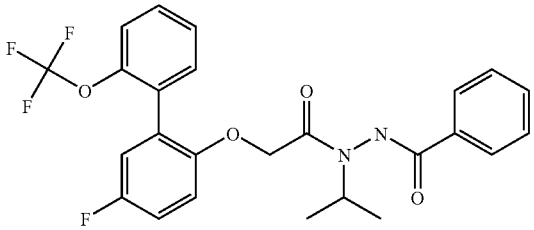

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated 2-trifluoromethoxybenzeneboronic acid (38 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was purified first on a silica gel column with a 20-30% ethyl acetate/hexanes gradient and then by RP HPLC to afford the product as a white solid (7 mg, 12%). MS m/e 491.19 $(M+H^+)$

Example 21

Preparation of benzoic acid N'-[2-(2'-ethoxy-5-fluoro-biphenyl-2-yloxy)-acetyl]-N'-isopropyl-hydrazide

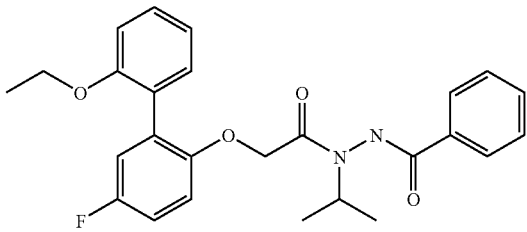

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-ethoxyphenylboronic acid (31 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate in hexanes gradient to afford the product as a white solid (16 mg, 29%). MS m/e 451.23 $(M+H^+)$

Example 22

Preparation of benzoic acid N'-[2-(5-fluoro-2'-isopropyl-biphenyl-2-yloxy)-acetyl]-N'-isopropyl-hydrazide

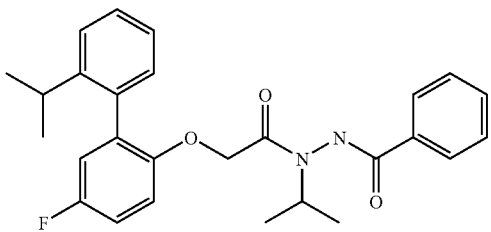

A solution of benzoic acid N'-[2-(2-bromo-4-fluoro-phenoxy)-acetyl]-N'-isopropyl-hydrazide (50 mg, 0.122 mmol) in DME (3 ml)/2M $Na_2CO_3$ (0.215 ml, 0.427 mmol) was treated with 2-isopropylphenylboronic acid (30 mg, 0.183 mmol) and $Pd[PPh_3]_4$ (28 mg, 0.0244 mmol) for 12 hours at 90° C. The reaction mixture was partitioned between water and ethyl acetate. The organic layer was washed with brine, dried over sodium sulfate, filtered, and concentrated. The crude was absorbed on silica and purified on a silica gel column with a 30-50% ethyl acetate/hexanes gradient to afford the product as a white, crystalline solid (30 mg, 55%). MS m/e 449.25 (M+H$^+$)

Example 23

Preparation of benzoic acid N'-[2-(5-fluoro-2'-methanesulfonyl-biphenyl-2-yloxy)-acetyl]-N'-isopropyl-hydrazide

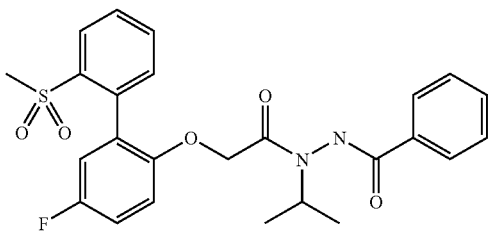

A solution of benzoic acid N'-[2-(5-fluoro-2'-methylsulfanyl-biphenyl-2-yloxy)-acetyl]-N'-isopropyl-hydrazide (30 mg, 0.066 mmol) in acetic acid (3 mL) was treated with 30% $H_2O_2$ (2 mL)) for 5.5 hours at 60° C. The reaction mixture was partitioned between water and ethyl acetate. The organic layer was washed with saturate sodium bicarbonate, brine, dried over sodium sulfate, filtered, and concentrated. The crude was absorbed on silica and purified on a silica gel column with a 30-50% ethyl acetate/hexanes gradient to afford the product as a white, crystalline solid (17 mg, 53%). MS m/e 485.28 (M+H$^+$)

Example 24

Preparation of benzoic acid N'-[2-(5,2',4'-trifluoro-biphenyl-2-yloxy)-acetyl]-N'-isopropyl-hydrazide

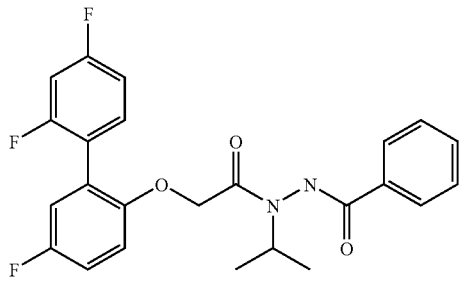

A solution of benzoic acid N'-[2-(2-bromo-4-fluoro-phenoxy)-acetyl]-N'-isopropyl-hydrazide (100 mg, 0.244 mmol) in DME (5 ml)/2M $Na_2CO_3$ (0.428 ml, 0.855 mmol) was treated with 2,4-difluorophenylboronic acid (77 mg, 0.489 mmol) and $Pd[PPh_3]_4$ (28 mg, 0.0244 mmol) at 90° C. overnight. The reaction mixture was partitioned between water and DCM. The organic layer was washed with brine, dried over sodium sulfate, filtered, and concentrated. The crude was absorbed on silica and purified on a silica gel column with a 30-50% ethyl acetate/hexanes gradient to afford the product as solid (90 mg, 82%). MS m/e 443.38 (M+H$^+$)

Example 25

Preparation of benzoic acid N'-[2-(5,4'-difluoro-4'-methyl-biphenyl-2-yloxy)-acetyl]-N'-isopropyl-hydrazide

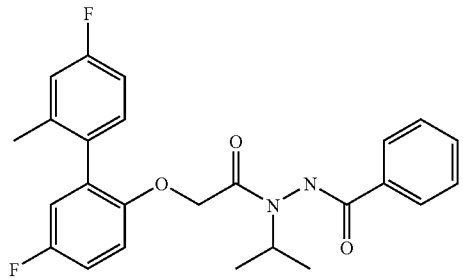

A solution of benzoic acid N'-[2-(2-bromo-4-fluoro-phenoxy)-acetyl]-N'-isopropyl-hydrazide (100 mg, 0.244 mmol) in DME (5 ml)/2M $Na_2CO_3$ (0.428 ml, 0.855 mmol) was treated with 4-fluoro-2-methylphenylboronic acid (75 mg, 0.489 mmol) and $Pd[PPh_3]_4$ (28 mg, 0.0244 mmol) at 90° C. overnight. The reaction mixture was partitioned between water and DCM. The organic layer was washed with brine, dried over sodium sulfate, filtered, and concentrated. The crude was absorbed on silica and purified on a silica gel column with a 30-50% ethyl acetate/hexanes gradient to afford the product as solid (69 mg, 63%). MS m/e 439.41 (M+H$^+$)

Example 26

Preparation of benzoic acid N'-[2-(2'-ethyl-5-methyl-biphenyl-2-yloxy)-acetyl]-N'-isopropyl-hydrazide

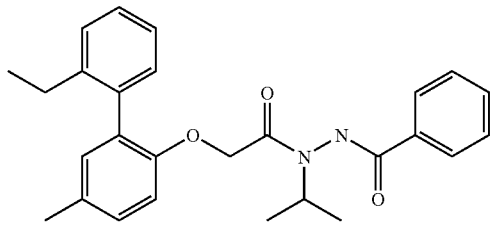

A solution of benzoic acid N'-[2-(2-bromo-4-methyl-phenoxy)-acetyl]-N'-isopropyl-hydrazide (100 mg, 0.247 mmol) in DME (3 ml)/2M $Na_2CO_3$ (0.435 ml, 0.8645 mmol) was treated with 2-ethylphenylboronic acid (74 mg, 0.493 mmol), $Pd[PPh_3]_4$ (29 mg, 0.0247 mmol in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate/hexanes gradient to afford the product as a white solid (77 mg, 72%). MS m/e 431.34 (M+H$^+$)

Example 27

Preparation of benzoic acid N'-[2-(2'-ethyl-4,5-difluoro-biphenyl-2-yloxy)-acetyl]-N'-isopropyl-hydrazide

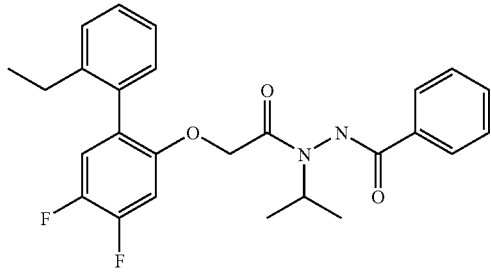

A solution of benzoic acid N'-[2-(2-bromo-4,5-difluorophenoxy)-acetyl]-N'-isopropyl-hydrazide (100 mg, 0.234 mmol) in DME (3 ml)/2M $Na_2CO_3$ (0.435 ml, 0.864 mmol) was treated with 2-ethylphenylboronic acid (70 mg, 0.468 mmol) and $Pd[PPh_3]_4$ (27 mg, 0.0234 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate in hexanes gradient to afford the product as a white solid (77 mg, 73%). MS m/e 453.30 (M+H$^+$)

Example 28

Preparation of benzoic acid N'-[2-(2'-ethyl-3,5-difluoro-biphenyl-2-yloxy)-acetyl]-N'-isopropyl-hydrazide

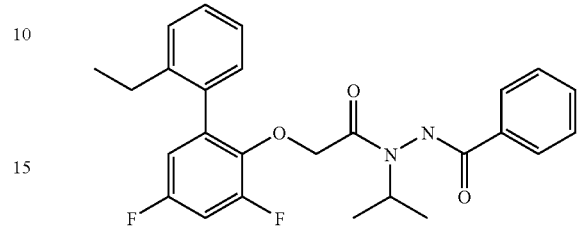

A solution of benzoic acid N'-[2-(2-bromo-4,6-difluorophenoxy)-acetyl]-N'-isopropyl-hydrazide (100 mg, 0.234 mmol) in DME (3 ml)/2M $Na_2CO_3$ (0.410 ml, 0.819 mmol) was treated with 2-ethylphenylboronic acid (71 mg, 0.468 mmol), and $Pd[PPh_3]_4$ (27 mg, 0.0234 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate/hexanes gradient to afford the product as a white solid (70 mg, 66%). MS m/e 453.30 (M+H$^+$)

Example 29

Preparation of benzoic acid N'-[2-(5-cyano-2'-ethyl-biphenyl-2-yloxy)-acetyl]-N'-isopropyl-hydrazide

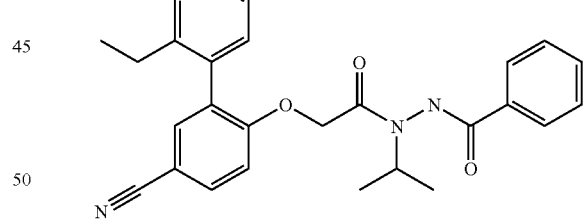

A solution of benzoic acid N'-[2-(2-bromo-4-cyano-phenoxy)-acetyl]-N'-isopropyl-hydrazide (200 mg, 0.480 mmol) in DME (3 ml)/2M $Na_2CO_3$ (0.840 ml, 1.68 mmol) was treated with 2-ethylphenylboronic acid (144 mg, 0.9608 mmol) and $Pd[PPh_3]_4$ (55 mg, 0.048 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with 30% ethyl acetate/hexanes to afford the product as a white solid (177 mg, 84%). MS m/e 442.25 (M+H$^+$)

Example 30

Preparation of 4-(2-methoxy-ethoxy)-benzoic acid N'-[2-(5-fluoro-2'-ethyl-biphenyl-2-yloxy)-acetyl]-N'-isopropyl hydrazide

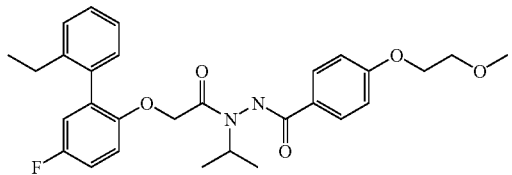

A solution of (2'-ethyl-5-fluoro-biphenyl-2-yloxy)-acetic acid (38 mg, 0.1395 mmol), and 4-(2-methoxy-ethoxy)-benzoic acid-N'-isopropyl hydrazide (32 mg, 0.1268 mmol) in DMF (5 mL), was treated with triethylamine (0.053 ml, 0.38 mmol), HOBT (20 mg, 0.152 mmol), and EDCI (29 mg, 0.152 mmol) for 12 hours at room temperature. The reaction mixture was partitioned between water and ethyl acetate. The organic layer was washed with brine, dried over sodium sulfate, filtered, and concentrated. The crude was absorbed on silica and purified on a silica gel column with a 50-100% ethyl acetate/hexanes gradient to afford the product as a white solid (5 mg, 7%). MS m/e 509.42 (M+H$^+$)

Example 31

Preparation of benzoic acid N'-[2-(5-methyl-2'-trifluoro-biphenyl-2-yloxy)-acetyl]-N'-isopropyl hydrazide

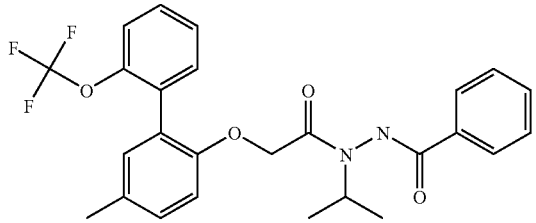

A solution of benzoic acid N'-[2-(2-bromo-4-methyl-phenoxy)-acetyl]-N'-isopropyl-hydrazide (100 mg, 0.234 mmol) in DME (3 mL)/2M Na$_2$CO$_3$ (0.443 ml, 0.863 mmol) was treated with 2-trifluoromethoxybenzeneboronic acid (76 mg, 0.370 mmol) and Pd[PPh$_3$]$_4$ (57 mg, 0.049 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate/hexanes gradient to afford the product as a white crystalline solid (89 mg, 74%). MS m/e 487.30 (M+H$^+$)

Example 32

Preparation of benzoic acid N'-[2-(4,5-difluoro-2'-trifluoromethoxy-biphenyl-2-yloxy)-acetyl]-N'-isopropyl hydrazide

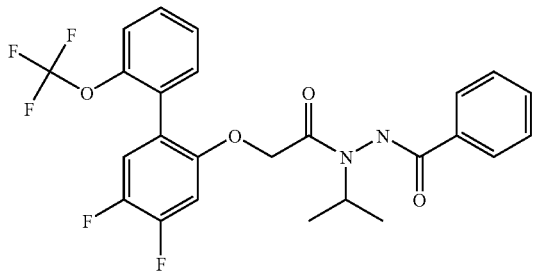

A solution of benzoic acid N'-[2-(2-bromo-4,5-difluoro-phenoxy)-acetyl]-N'-isopropyl-hydrazide (100 mg, 0.234 mmol) in DME (3 ml)/2M Na$_2$CO$_3$ (0.443 ml, 0.863 mmol) was treated with 2-trifluoromethoxybenzeneboronic acid (72 mg, 0.351 mmol) and Pd[PPh$_3$]$_4$ (54 mg, 0.046 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate in hexanes gradient to afford the product as a white, crystalline solid (81 mg, 68%). MS m/e 509.24 (M+H$^+$)

Example 33

Preparation of benzoic acid N'-[2-(3,5-difluoro-2'-trifluoromethoxy-biphenyl-2-yloxy)-acetyl]-N'-isopropyl hydrazide

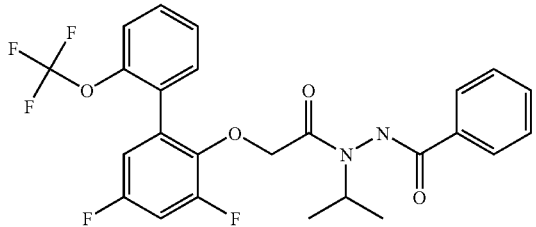

A solution of benzoic acid N'-[2-(2-bromo-4,6-difluoro-phenoxy)-acetyl]-N'-isopropyl-hydrazide (100 mg, 0.234 mmol) in DME (3 ml)/2M Na$_2$CO$_3$ (0.410 ml, 0.819 mmol) was treated with 2-trifluoromethoxybenzeneboronic acid (72 mg, 0.351 mmol) and Pd[PPh$_3$]$_4$ (54 mg, 0.046 mmol) in a microwave oven at 150° C. for 10 min. The reaction mixture was partitioned between water and ethyl acetate. The organic layer was washed with brine, dried over sodium sulfate, filtered, and concentrated. The crude was absorbed on silica and purified on a silica gel column with a 20-40% ethyl acetate/hexanes gradient to afford the product as a white crystalline solid (70 mg, 59%). MS m/e 509.24 (M+H$^+$)

Example 34

Preparation of tetrahydro-pyran-4-carboxylic-acid-N'-[2-(5-fluoro-2'-trifluoromethoxy-biphenyl-2-yloxy)-acetyl]-N'-isopropyl-hydrazide

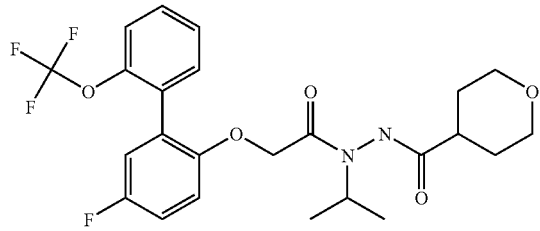

A solution of (5-fluoro-2'-trifluoromethoxy-biphenyl-2-yloxy)-acetic acid (280 mg, 0.85 mmol) and tetrahydro-pyran-4-carboxylic acid N'-isopropyl-hydrazide (1.2 eq. 190 mg, 1.02 mmol) in DMF (3 ml) was treated with diisopropyl amine (0.370 ml, 2.12 mmol) and PyBroP (595 mg, 1.275 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 50-100% ethyl acetate/hexanes gradient to afford the product as a white solid (262 mg, 62%). MS m/e 499.23 (M+H$^+$)

Example 35

Preparation of 3-methyl-furan-2-carboxylic acid N'-[2-(5-fluoro-2'-trifluoromethoxy-biphenyl-2-yloxy)-acetyl]-N'-isopropyl-hydrazide

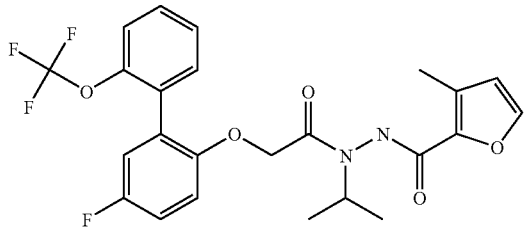

A solution of (5-fluoro-2'-trifluoromethoxy-biphenyl-2-yloxy)-acetic acid (211 mg, 0.64 mmol) and 3-methyl-furan-2-carboxylic acid N'-isopropyl-hydrazide (140 mg, 0.768 mmol) in DMF (3 ml) was treated with diisopropyl amine (0.278 ml, 1.6 mmol) and PyBroP (448 mg, 0.96 mmol) at room temperature overnight. The reaction mixture was partitioned between 1N HCl and ethyl acetate. The organic layer was successively washed with saturated sodium bicarbonate and brine, then dried over sodium sulfate, filtered and concentrated. The crude was absorbed on silica and purified on a silica gel column with a 50-100% ethyl acetate in hexanes gradient to afford the product as a white solid (180 mg, 57%). MS m/e 495.19 (M+H$^+$)

Example 36

Preparation of furan-2-carboxylic acid N'-[2-(5-fluoro-2'-trifluoromethoxy-biphenyl-2-yloxy)-acetyl]-N'-isopropyl-hydrazide

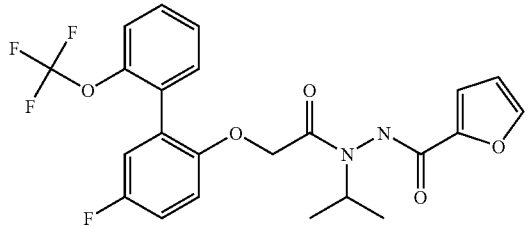

A solution of (5-fluoro-2'-trifluoromethoxy-biphenyl-2-yloxy)-acetic acid (174 mg, 0.52 mmol) and furan-2-carboxylic acid N'-isopropyl-hydrazide (90 mg, 0.53 mmol) in DMF (5 ml) was treated with diisopropyl amine (0.235 ml, 1.32 mmol) and PyBroP (370 mg, 0.79 mmol) at room temperature overnight. The reaction mixture was partitioned between saturated aqueous sodium bicarbonate and ethyl acetate. The organic layer was successively washed with water and brine, then dried over sodium sulfate, filtered and concentrated. The crude was absorbed on silica and purified on a silica gel column with a 30-80% ethyl acetate in hexanes gradient to afford the product as a white solid (110 mg, 44%). MS m/e 481.38 (M+H$^+$)

Example 37

Preparation of furan-3-carboxylic acid N'-[2-(5-fluoro-2'-trifluoromethoxy-biphenyl-2-yloxy)-acetyl]-N'-isopropyl-hydrazide

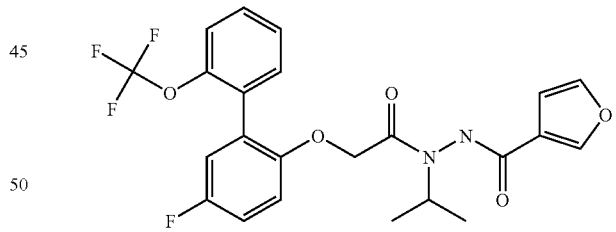

A solution of (5-fluoro-2'-trifluoromethoxy-biphenyl-2-yloxy)-acetic acid (180 mg, 0.54 mmol) and furan-3-carboxylic acid N'-isopropyl-hydrazide (110 mg, 0.65 mmol) in DMF (5 ml) was treated with diisopropyl amine (0.237 ml, 1.36 mmol) and PyBroP (381 mg, 0.82 mmol) at room temperature overnight. The reaction mixture was partitioned between 1N HCl and ethyl acetate. The organic layer was successively washed with aqueous saturated sodium bicarbonate and brine, then dried over sodium sulfate, filtered and concentrated. The crude was absorbed on silica and purified on a silica gel column with a 30-50% ethyl acetate in hexanes gradient to afford the product as a solid (145 mg, 56%). MS m/e 481.35 (M+H$^+$)

Example 38

Preparation of cyclohexanecarboxylic acid N'-[2-(5-fluoro-2'-trifluoromethoxy-biphenyl-2-yloxy)-acetyl]-N'-isopropyl-hydrazide

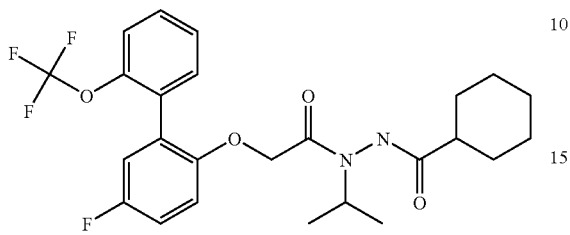

A solution of cyclohexanecarboxylic acid N'-[2-(2-bromo-4-fluoro-phenoxy)-acetyl]-N'-isopropyl-hydrazide (310 mg, 0.75 mmol) in DME (3 ml)/2M $Na_2CO_3$ (1.3 ml, 2.62 mmol) was treated 2-trifluoromethoxybenzeneboronic acid (231 mg, 1.12 mmol) and $Pd[PPh_3]_4$ (172 mg, 0.15 mmol) in a microwave oven at 150° C. for 10 min. The reaction mixture was partitioned between water and ethyl acetate. The organic layer was washed with brine, dried over sodium sulfate, filtered, and concentrated. The crude was purified first on a silica gel column with a 30-80% ethyl acetate/hexanes gradient to afford the product as a solid (232 mg, 63%). MS m/e 497.53 (M+H$^+$)

Example 39

Preparation of 4-(2-methoxy-ethoxy)-benzoic acid N'-[2-(5-fluoro-2'-trifluoromethoxy-biphenyl-2-yloxy)-acetyl]-N'-isopropyl hydrazide

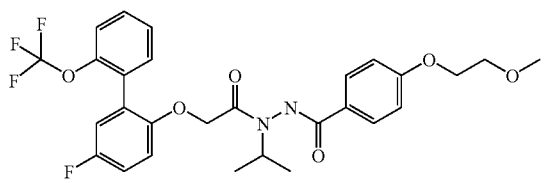

A solution of 4-(2-methoxy-ethoxy)-benzoic acid N'-[2-(2-bromo-4-fluoro-phenoxy)-acetyl]-N'-isopropyl-hydrazide (202 mg, 0.42 mmol) in DME (5 ml)/2M $Na_2CO_3$ (0.731 ml, 1.46 mmol) was with 2-trifluoromethoxyphenylboronic acid (129 mg, 0.63 mmol) and $Pd[PPh_3]_4$ (96.5 mg, 0.084 mmol) in a microwave oven at 150° C. for 10 min. The reaction mixture was partitioned between water and DCM. The organic layer was washed with brine, dried over sodium sulfate, filtered, and concentrated. The crude was adsorbed on silica and purified on a silica gel column with a 45-60% ethyl acetate/hexane gradient to afford the product as a solid (129 mg, 55%). MS m/e 565.55 (M+H$^+$)

Example 40

Preparation of thiophene-2-carboxylic acid N'-[2-(5-fluoro-2'-trifluoromethoxy-biphenyl-2-yloxy)-acetyl]-N'-isopropyl hydrazide

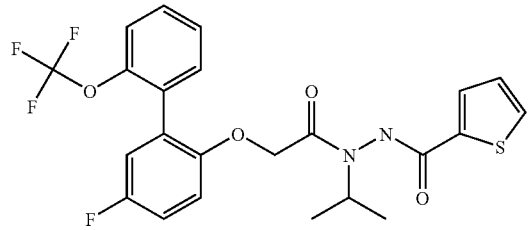

A solution of thiophene-2-carboxylic acid N'-[2-(2-bromo-4-fluoro-phenoxy)-acetyl]-N'-isopropyl-hydrazide (263 mg, 0.63 mmol) in DME (5 ml)/2M $Na_2CO_3$ (1.10 ml, 2.22 mmol) was with 2-trifluoromethoxyphenylboronic acid (196 mg, 0.95 mmol) and $Pd[PPh_3]_4$ (146 mg, 0.13 mmol) in a microwave oven at 150° C. for 10 min. The reaction mixture was partitioned between water and DCM. The organic layer was washed with brine, dried over sodium sulfate, filtered, and concentrated. The crude was adsorbed on silica and purified on a silica gel column with a 30-50% ethyl acetate/hexane gradient to afford the product as a solid (176 mg, 56%). MS m/e 497.41 (M+H$^+$)

Example 41

Preparation of tetrahydro-thiopyran-4-carboxylic acid N'-[2-(5-fluoro-2'-trifluoromethoxy-biphenyl-2-yloxy)-acetyl]-N'-isopropyl hydrazide

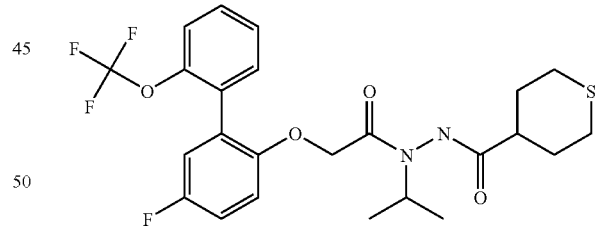

A solution of tetrahydro-thiopyran-4-carboxylic acid N'-[2-(2-bromo-4-fluoro-phenoxy)-acetyl]-N'-isopropyl-hydrazide (116 mg, 0.27 mmol) in DME (2.5 ml)/2M $Na_2CO_3$ (0.468 ml, 0.94 mmol) was treated with 2-trifluoromethoxyphenylboronic acid (83 mg, 0.40 mmol) and $Pd[PPh_3]_4$ (62 mg, 0.053 mmol) in a microwave oven at 150° C., for 10 min. The reaction mixture was partitioned between water and dichloromethane. The organic layer was washed with brine, dried over sodium sulfate, filtered, and concentrated. The crude was adsorbed on silica and purified on a silica gel column with a 30-50% ethyl acetate/hexane gradient to afford the product as a solid (62.6 mg, 45%). MS m/e 515.48 (M+H$^+$)

Example 42

Preparation of thiophene-3-carboxylic acid N'-[2-(5-fluoro-2'-trifluoromethoxy-biphenyl-2-yloxy)-acetyl]-N'-isopropyl hydrazide

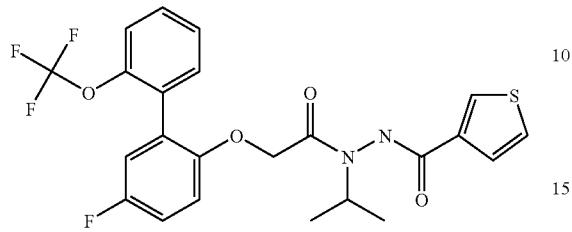

A solution of thiophene-3-carboxylic acid N'-[2-(2-bromo-4-fluoro-phenoxy)-acetyl]-N'-isopropyl-hydrazide (251 mg, 0.60 mmol) in DME (5 ml)/2M Na₂CO₃ (1.05 ml, 2.12 mmol) was with 2-trifluoromethoxyphenylboronic acid (187 mg, 0.91 mmol) and Pd[PPh₃]₄ (140 mg, 0.12 mmol) in a microwave oven at 150° C. for 10 min. The reaction mixture was partitioned between water and DCM. The organic layer was washed with brine, dried over sodium sulfate, filtered, and concentrated. The crude was adsorbed on silica and purified on a silica gel column with a 30-50% ethyl acetate/hexane gradient to afford the product as a solid (188 mg, 63%). MS m/e 497.41 (M+H$^+$)

Example 43

Preparation of thiophene-3-carboxylic acid N'-[2-(5-fluoro-2'-ethyl-biphenyl-2-yloxy)-acetyl]-N'-isopropyl hydrazide

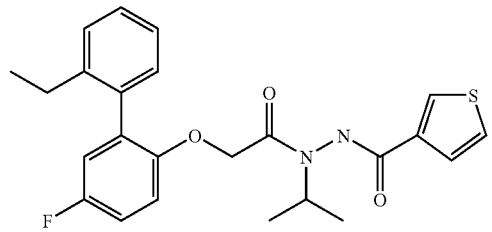

A solution of (2'-ethyl-5-fluoro-biphenyl-2-yloxy)-acetic acid (100 mg, 0.36 mmol), and tiophehe-3-carboxylic acid-N'-isopropyl hydrazide (32 mg, 0.1268 mmol) in DMF (5 mL), was treated with triethylamine (0.152 ml, 1.09 mmol), HOBT (59 mg, 0.44 mmol), and EDCI (84 mg, 0.44 mmol) for 12 hours at room temperature. The reaction mixture was partitioned between 1N HCl and DCM. The organic layer was successively washed with 1N NaOH and brine, then dried over sodium sulfate, filtered, and concentrated. The crude was absorbed on silica and purified on a silica gel column with a 30-50% ethyl acetate/hexanes gradient to afford the product as a solid (41 mg, 26%). MS m/e 441.30 (M+H$^+$)

Example 44

Preparation of benzoic acid N'-[2-(2-cyclopentyl-phenoxy)-acetyl]-N'-isopropyl-hydrazide

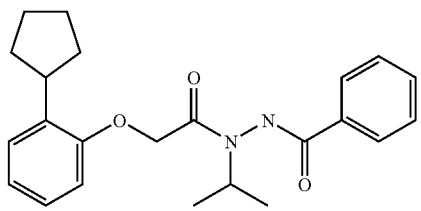

A solution of (2-cyclopenyl-phenoxy)-acetic acid (203 mg, 0.92 mmol), and benzoic acid N'-isopropyl-hydrazide (150 mg, 0.842 mmol) in DMF (5 ml), was treated with triethylamine (0.352 ml, 2.52 mmol), HOBT (136 mg, 1.00 mmol), and EDCI (194 mg, 1.00 mmol) for 12 hours at room temperature. The reaction mixture was partitioned between 1N HCl and DCM. The organic layer was successively washed with 1N NaOH and brine, then dried over sodium sulfate, filtered, and concentrated. The crude was absorbed on silica and purified on a silica gel column with 50% ethyl acetate/hexanes to afford the product as a white solid (123 mg, 35%). MS m/e 381.33 (M+H$^+$)

Example 45

Preparation of benzoic acid N'-[2-(2-sec-butyl-phenoxy)-acetyl]-N'-isopropyl-hydrazide

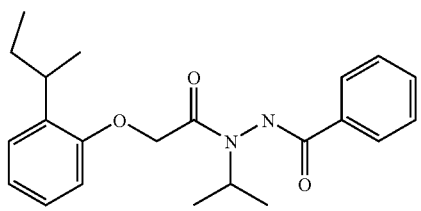

A solution of (2-sec-butyl-phenoxy)-acetic acid (193 mg, 0.93 mmol), and benzoic acid N'-isopropyl-hydrazide (150 mg, 0.842 mmol) in DMF (5 ml), was treated with triethylamine (0.352 ml, 2.52 mmol), HOBT (136 mg, 1.00 mmol), and EDCI (194 mg, 1.00 mmol) for 12 hours at room temperature. The reaction mixture was partitioned between 1N HCl and DCM. The organic layer was successively washed with 1N NaOH and brine, then dried over sodium sulfate, filtered, and concentrated. The crude was absorbed on silica and purified on a silica gel column with 50% ethyl acetate/hexanes to afford the product as a white solid (113 mg, 33%). MS m/e 369.32 (M+H$^+$)

Example 46

Preparation of benzoic acid N'-[2-(2-propyl-phenoxy)-acetyl]-N'-isopropyl-hydrazide

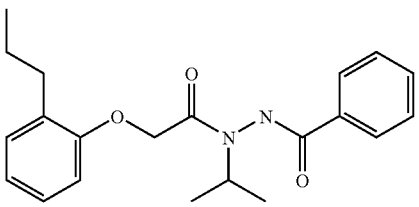

A solution of (2-propyl-phenoxy)-acetic acid (180 mg, 0.93 mmol), and benzoic acid N'-isopropyl-hydrazide (150 mg, 0.842 mmol) in DMF (5 ml), was treated with triethylamine (0.352 ml, 2.52 mmol), HOBT (136 mg, 1.00 mmol), and EDCI (194 mg, 1.00 mmol) for 12 hours at room temperature. The reaction mixture was partitioned between 1N HCl and DCM. The organic layer was successively washed with 1N NaOH and brine, then dried over sodium sulfate, filtered, and concentrated. The crude was absorbed on silica and purified on a silica gel column with 10% ethyl acetate/hexanes to afford the product as a white solid (80 mg, 25%). MS m/e 355.35 (M+H+)

Example 47

Preparation of benzoic acid N'-[2-(2-benzyl-phenoxy)-acetyl]-N'-isopropyl-hydrazide

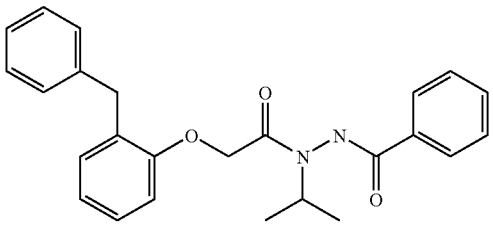

A solution of (2-benzyl-phenoxy)-acetic acid (1.15 g, 4.74 mmol), and benzoic acid N'-isopropyl-hydrazide (704 mg, 3.95 mmol) in DMF (30 ml), was treated with diisopropyl ethyl amine (1.8 ml, 9.88 mmol), and PyBroP (2.76 g, 5.93 mmol) for 12 hours at room temperature. The reaction mixture was partitioned between 1N HCl and DCM. The organic layer was successively washed brine, dried over sodium sulfate, filtered, and concentrated. The crude was absorbed on silica and purified on a silica gel column with 50% ethyl acetate/hexanes to afford the product as a white solid (950 mg, 60%). MS m/e 403.25 (M+H+)

Example 48

Preparation of benzoic acid N'-[2-(3'-fluoro-biphenyl-2-ylsulfanyl)-acetyl]-N'-isopropyl-hydrazide

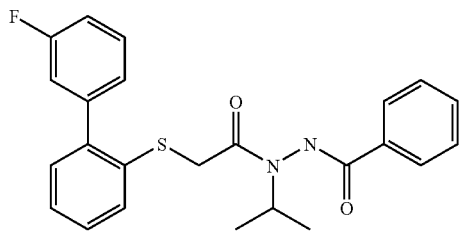

A solution of benzoic acid N'-[2-(2-bromo-phenylsulfanyl)-acetyl]-N'-isopropyl-hydrazide (50 mg, 0.123 mmol) in DME (4 ml)/2M Na$_2$CO$_3$ (0.645 ml, 1.29 mmol) was treated with 3-fluorophenylboronic acid (34.4 mg, 0.246 mmol) and Pd[PPh$_3$]$_4$ (70.2 mg, 0.061 mmol) for 65 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient. Further purification by RP HPLC afforded the product (8.7 mg, 16.7%). MS m/e 423.21 (M+H+)

Example 49

Preparation of benzoic acid N'-[2-(2',3'-dimethyl-biphenyl-2-ylsulfanyl)-acetyl]-N'-isopropyl-hydrazide

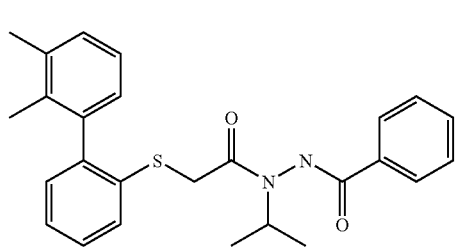

A solution of benzoic acid N'-[2-(2-bromo-phenylsulfanyl)-acetyl]-N'-isopropyl-hydrazide (50 mg, 0.123 mmol) in DME (4 ml)/2M Na$_2$CO$_3$ (0.645 ml, 1.29 mmoles) was treated with 2,3-dimethylphenylboronic acid (36.9 mg, 0.246 mmol) and Pd[PPh$_3$]$_4$ (70.2 mg, 0.061 mmol) for 65 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient. Further purification by RP HPLC afforded the product (8.5 mg, 16.4%). MS m/e 433.24 (M+H+)

Example 50

Preparation of benzoic acid N'-[2-(3'-methoxy-biphenyl-2-ylsulfanyl)-acetyl]-N'-isopropyl-hydrazide

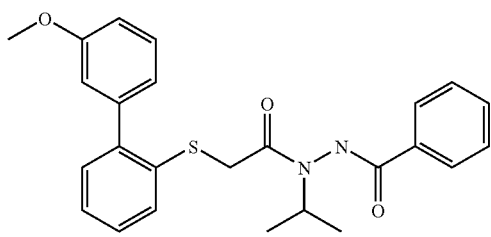

A solution of benzoic acid N'-[2-(2-bromo-phenylsulfanyl)-acetyl]-N'-isopropyl-hydrazide (100 mg, 0.246 mmol) in DME (5 ml)/2M $Na_2CO_3$ (0.430 ml, 0.86 mmoles) was treated with 3-methoxyphenylboronic acid (75 mg, 0.491 mmol) and Pd[$PPh_3$]$_4$ (29 mg, 0.025 mmol) for 18 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient to afford the product as a solid (58 mg, 55%). MS m/e 435.22 (M+H$^+$)

Example 51

Preparation of benzoic acid N'-[2-(4'-fluoro-biphenyl-2-ylsulfanyl)-acetyl]-N'-isopropyl-hydrazide

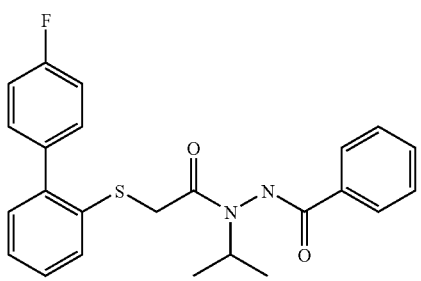

A solution of benzoic acid N'-[2-(2-bromo-phenylsulfanyl)-acetyl]-N'-isopropyl-hydrazide (50 mg, 0.123 mmol) in DME (4 ml)/2M $Na_2CO_3$ (0.215 ml, 0.43 mmoles) was treated with 4-fluorophenylboronic acid (35 mg, 0.25 mmol) and Pd[$PPh_3$]$_4$ (14 mg, 0.012 mmol) for 12 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient. Further purification by RP HPLC afforded the product (9.5 mg, 20%). MS m/e 423.22 (M+H$^+$)

Example 52

Preparation of benzoic acid N'-[2-(3'-trifluoromethyl-biphenyl-2-ylsulfanyl)-acetyl]-N'-isopropyl-hydrazide

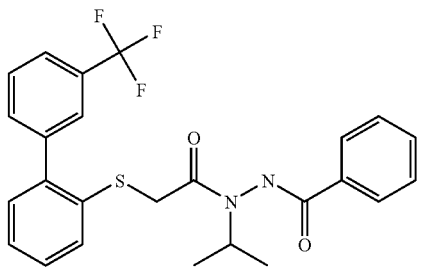

A solution of benzoic acid N'-[2-(2-bromo-phenylsulfanyl)-acetyl]-N'-isopropyl-hydrazide (50 mg, 0.123 mmol) in DME (4 ml)/2M $Na_2CO_3$ (0.215 ml, 0.43 mmoles) was treated with 3-trifluoromethylphenylboronic acid (47 mg, 0.25 mmol) and Pd[$PPh_3$]$_4$ (14 mg, 0.012 mmol) for 12 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient. Further purification by RP HPLC afforded the product (8 mg, 14%). MS m/e 473.16 (M+H$^+$)

Example 53

Preparation of benzoic acid N'-[2-(2'-methoxy-biphenyl-2-ylsulfanyl)-acetyl]-N'-isopropyl-hydrazide

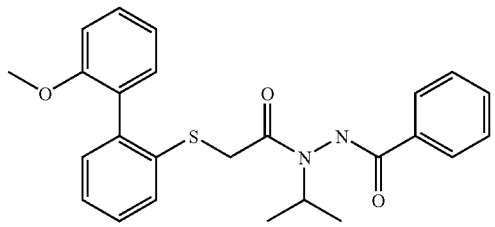

A solution of benzoic acid N'-[2-(2-bromo-phenylsulfanyl)-acetyl]-N'-isopropyl-hydrazide (100 mg, 0.246 mmol) in DME (5 ml)/2M $Na_2CO_3$ (0.43 ml, 0.86 mmoles) was treated with 2-methoxyphenylboronic acid (75 mg, 0.49 mmol) and Pd[$PPh_3$]$_4$ (28 mg, 0.025 mmol) for 12 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient to afford the product as a solid (59 mg, 54%). MS m/e 435.23 (M+H$^+$)

Example 54

Preparation of benzoic acid N'-[2-(2'-fluoro-biphenyl-2-ylsulfanyl)-acetyl]-N'-isopropyl-hydrazide

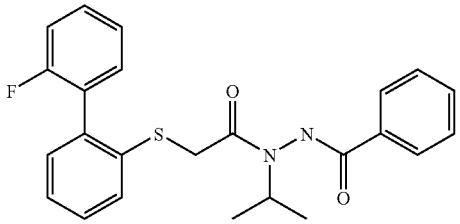

A solution of benzoic acid N'-[2-(2-bromo-phenylsulfanyl)-acetyl]-N'-isopropyl-hydrazide (100 mg, 0.246 mmol) in DME (5 ml)/2M Na$_2$CO$_3$ (0.43 ml, 0.86 mmoles) was treated with 2-fluorophenylboronic acid (69 mg, 0.49 mmol) and Pd[PPh$_3$]$_4$ (28 mg, 0.025 mmol) for 12 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient to afford the product as a solid (72 mg, 68%). MS m/e 423.22 (M+H$^+$)

Example 55

Preparation of benzoic acid N'-[2-(4'-methoxy-biphenyl-2-ylsulfanyl)-acetyl]-N'-isopropyl-hydrazide

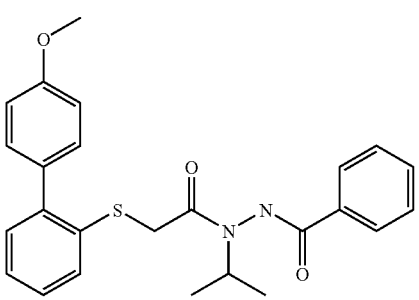

A solution of benzoic acid N'-[2-(2-bromo-phenylsulfanyl)-acetyl]-N'-isopropyl-hydrazide (100 mg, 0.246 mmol) in DME (5 ml)/2M Na$_2$CO$_3$ (0.43 ml, 0.86 mmoles) was treated with 4-methoxyphenylboronic acid (75 mg, 0.49 mmol) and Pd[PPh$_3$]$_4$ (28 mg, 0.025 mmol) for 12 hours at 90° C. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient to afford the product as a solid (78 mg, 72%). MS m/e 435.24 (M+H$^+$)

Example 56

Preparation of benzoic acid N'-[2-(biphenyl-2-ylsulfanyl)-acetyl]-N'-isopropyl-hydrazide

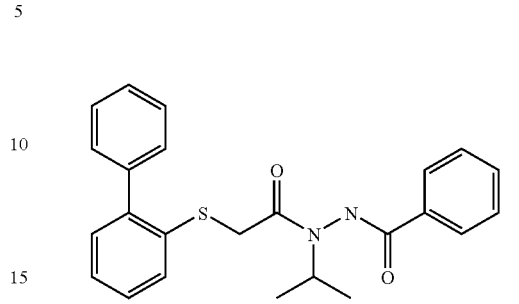

A solution of benzoic acid N'-[2-(2-bromo-phenylsulfanyl)-acetyl]-N'-isopropyl-hydrazide (50 mg, 0.123 mmol) in DME (4 ml)/2M Na$_2$CO$_3$ (0.215 ml, 0.43 mmoles) was treated with phenylboronic acid (30 mg, 0.25 mmol) and Pd[PPh$_3$]$_4$ (14 mg, 0.012 mmol) for 12 hours at 90° C. Additional amounts of Pd[PPh$_3$]$_4$ (28 mg, 0.025 mmol) and 2M Na$_2$CO$_3$ (0.215 ml, 0.43 mmoles) were added and the mixture was stirred at 90° C. for another night. The reaction mixture was partitioned between water and DCM. The organic layer was washed with brine, dried over sodium sulfate, filtered, and concentrated. The crude was adsorbed on silica and purified on a silica gel column with a 20-50% ethyl acetate/hexane gradient. Further purification by RP HPLC afforded the product (7.2 mg, 15%). MS m/e 405.26 (M+H$^+$)

Example 57

Preparation of 4-(isobutylamino)-benzoic acid N'-[2-(5-fluoro-2'-trifluoromethoxy-biphenyl-2-yloxy)-acetyl]-N'-isopropyl hydrazide

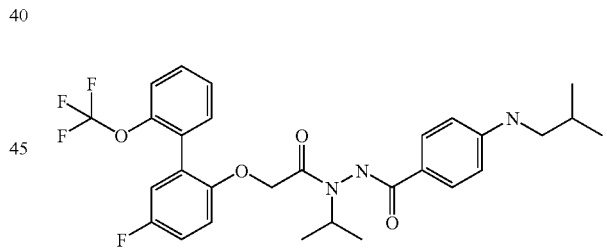

A solution of 4-nitro-benzoic acid N'-isopropyl-hydrazide (84 mg, 0.378 mmol), (5-fluoro-2'-trifluoromethoxy-biphenyl-2-yloxy)-acetic acid (100 mg, 0.302 mmol), and DIPEA (0.329 ml, 1.89 mmol) in DMF (5 ml) was treated with PyBroP (176 mg, 0.378 mmol) and let stir at 25° C. overnight. The reaction mixture was diluted with 70 ml ethyl acetate and extracted with 1N HCl (2×30 ml), saturated sodium bicarbonate (2×30 ml). The organic layer was dried over sodium sulfate, filtered, and concentrated to a gum (150 mg). The crude material (75 mg, 0.14 mmol) dissolved in EtOH (5 ml) containing acetic acid (2 drops), concentrated HCl (20 μl), isobutyraldehyde (152 μl, 1.68 mmol) and 10% palladium on carbon (10 mg) This mixture was hydrogenated at 20 psi at rt for 5 hours. The reaction mixture was filtered through celite diluted with ethyl acetate, washed with saturated sodium bicarbonate, dried over sodium sulfate, filtered and concentrated. The crude product was triturated with 1% ethyl acetate/hexanes to give an off-white solid (31 mg, 39%). MS m/e 562 (M+H$^+$)

Example 58

DGAT Phospholipid FlashPlate Assay

Materials for the assay: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet (in house preparation), with a protein concentration of 9.85 mg/ml.

Aqueous buffers were prepared or purchased as follows: The coating buffer (CB) was purchased from PerkinElmer, catalog number SMP900A; the reaction buffer (RB) was 50 mM Tris-HCl, pH 7.5, 100 mM NaCl, 0.01% BSA in water; the washing buffer (WB) was 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 µM with coating buffer (CB). The diluted DAG solution was then added to 384-well PL-FlashPlates at 60 µl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 µM in 100% DMSO. Diluted compound were further diluted 10 fold with reaction buffer (RB). $^{14}$C-Pal-CoA was diluted to 8.3 µM with RB. The DGAT pellet was diluted to 0.13 mg protein/ml with dilution buffer (DB) immediately before it was added to the PL-FlashPlates to start the reaction. 20 µl of the RB-diluted compounds (or 10% DMSO in RB for Total and Blank), 15 µl of RB diluted 14C-Pal-CoA and 15 µl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of IC$_{50}$: The IC$_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

(A+((B−A)/(1+((x/C)$^\wedge$D))))

with A and B as the bottom and top of the curve (highest and lowest inhibition), respectively, and C as IC$_{50}$ and D as Hill Coefficient of the compound. The results are summarized in Table 1:

TABLE 1

| Compound of Example | Activity in DGAT Phospholipid FlashPlate Assay (A = IC$_{50}$ < 0.3 µM, B = IC$_{50}$ < 1 µM) |
|---|---|
| 1 | A |
| 2 | B |

TABLE 1-continued

| Compound of Example | Activity in DGAT Phospholipid FlashPlate Assay (A = IC$_{50}$ < 0.3 µM, B = IC$_{50}$ < 1 µM) |
|---|---|
| 3 | A |
| 4 | A |
| 5 | A |
| 6 | B |
| 7 | B |
| 8 | B |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | B |
| 24 | A |
| 25 | B |
| 26 | A |
| 27 | A |
| 28 | A |
| 29 | B |
| 30 | A |
| 31 | A |
| 32 | A |
| 33 | A |
| 34 | A |
| 35 | B |
| 36 | B |
| 37 | A |
| 38 | A |
| 39 | A |
| 40 | A |
| 41 | A |
| 42 | A |
| 43 | B |
| 44 | B |
| 45 | B |
| 46 | B |
| 47 | B |
| 48 | A |
| 49 | A |
| 50 | A |
| 51 | A |
| 52 | A |
| 53 | A |
| 54 | A |
| 55 | A |
| 56 | A |
| 57 | A |

Example 59

DGAT CHOK1 Cell Assay

Materials for the assay were: petroleum ether (J. T. Baker #9268-22); diethyl ether (Aldrich #30995-8); acetic acid; 1,2-dioleoyl-3-palmitoyl-glycerol (Sigma D-1782); $^{14}$D Palmitic Acid (56.0 mCi/mmol PerkinElmer Life Sciences # NEC 075H); DMEM/F12 (Gibco #11330-032); fetal bovine serum; L-Glutamine; G418/ml media; DMEM High Glucose (Gibco #11995-065); BSA Fraction V Fatty Acid Free (Roche #100 377); 20×°cm silica gel 60 glass plates (EM Science Plates #5721/7).

CHOK1/DGAT cell culture medium was prepared with DMEM/F12 (Gibco #11330-032), 10% 1% L-Glutamine, and 20 ul G418/ml media. 1,2-dioleoyl-3-palmitoyl-glycerol was prepared by dissolving 10 mg into 1 ml chloroform and stored at −20° C. in 100 μl aliquots. Test compounds were prepared as 10 mM stock solutions in DMSO and store at −20° C. before use. Test dilutions were prepared by five fold serial dilutions over final concentrations.

CHOK1 cells transfected with DGAT1 were diluted in 6 well plates at $2.5 \times 10^5$ cells per well and cultured overnight. Cells were then washed twice with PBS. Test compound solutions (10 μl/2 ml media aliquots) in DMEM High Glucose with 0.01% BSA (fatty acid free) were added to cell culture plates at 800 μl per well. $^{14}$C Palmitic acid (0.5 μCi, 5 μl) was added to each well. The plates were incubated for 1 hour at 37° C. After the incubation period, the plates were placed on ice, cells were scraped into media and transferred to microfuge tubes. 400 μl chloroform:methanol (2:1) was added to each tube. Each tube was briefly vortexed by hand, then mechanically vortexed for 10 minutes. Each tube was then centrifuged at 14,000 RPM for 10 minutes at 4° C. and the bottom layer removed and transferred to a new microfuge tube.

Extracted samples were spotted onto TLC plates at 20 μl per lane. The TLC plates were eluted with a solvent mixture of petroleum ether, diethyl ether and acetic acid (80:20:1) and air dried. Trigylceride (TG) spots were visualized by placing in an iodine chamber for several minutes. 1 μl of $^{14}$C palmitic acid (diluted 1:10 in 100% EtOH) was spotted on the TG standard lane (at TG level) as a reference. The TLC plates were wrapped in plastic wrap and placed in a phosphorimager cassette for scanning.

Calculation of $EC_{50}$

The $EC_{50}$ values for those compounds tested in this Example were generated using an Excel template, the results of which are shown in Table II:

TABLE II

| Compound of Example | EC50 (μM) | Activity in DGAT Assay (A = $IC_{50}$ < 3 μM, B = $IC_{50}$ < 40 μM) |
|---|---|---|
| 1 | 8.3 | B |
| 2 | 3.1 | B |
| 3 | 1.02 | A |
| 4 | 1.81 | A |
| 5 | 2.21 | A |
| 9 | 3.78 | B |
| 10 | 0.91 | A |
| 11 | 1.85 | A |
| 12 | 1.01 | A |
| 13 | 0.31 | A |
| 14 | 0.23 | A |
| 15 | 4.86 | B |
| 16 | 0.216 | A |
| 17 | 2.17 | A |
| 18 | 2.69 | A |
| 19 | 1.3 | A |
| 20 | 0.328 | A |
| 21 | 1.34 | A |
| 22 | 0.38 | A |
| 24 | 2.93 | A |
| 25 | 1.368 | A |
| 26 | 0.88 | A |
| 27 | 2.1 | A |
| 28 | 0.296 | A |
| 29 | 1.369 | A |
| 30 | 1.829 | A |
| 31 | 0.776 | A |
| 32 | 0.938 | A |

TABLE II-continued

| Compound of Example | EC50 (μM) | Activity in DGAT Assay (A = $IC_{50}$ < 3 μM, B = $IC_{50}$ < 40 μM) |
|---|---|---|
| 33 | 0.356 | A |
| 34 | 1.244 | A |
| 37 | 11.11 | B |
| 38 | 2.815 | A |
| 39 | 3.054 | B |
| 40 | 3.479 | B |
| 41 | 0.774 | A |
| 42 | 3.294 | B |
| 48 | 3.4 | B |
| 49 | 5.67 | B |
| 50 | 1.29 | A |
| 51 | 4.9 | B |
| 52 | 1.6 | A |
| 53 | 6.7 | B |
| 54 | 1.43 | A |
| 55 | 2.3 | A |
| 56 | 37.41 | B |
| 57 | 0.348 | A |

It is to be understood that the invention is not limited to the particular embodiments of the invention described above, as variations of the particular embodiments may be made and still fall within the scope of the appended claims.

What is claimed is:

1. A compound of the formula (I):

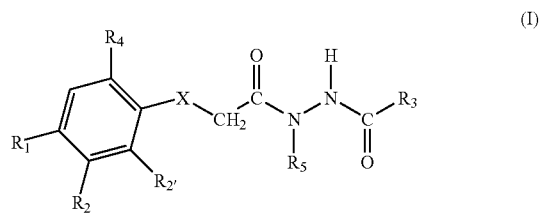

wherein:

X is O or S;

$R_1$ is hydrogen, halogen, ($C_1$-$C_6$)alkyl or cyano;

$R_2$, $R_{2'}$ are independently of each other H or halogen;

$R_3$ is unsubstituted phenyl, phenyl substituted with a group independently selected from the group consisting of halogen, ($C_1$-$C_6$) alkyl, $NH(CH_2)_nCH(CH_3)_2$, or —$O(CH_2)_nOCH_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocycyl substituted with ($C_1$-$C_6$) alkyl, or substituted or unsubstituted 5-10-membered carbocyclic ring;

$R_4$ is branched or unbranched ($C_2$-$C_6$) alkyl, unsubstituted phenyl, phenyl mono-, di- or tri-substituted with a group independently selected from the group consisting of halogen, ($C_1$-$C_6$) alkyl, ($C_1$-$C_6$) alkoxy, —O(CH)($CH_3$)$_2$, —$CF_3$, —$O(CH_2)_nCH_3$, —$OCF_3$, —$SCH_3$, —$SO_2CH_3$, —$NO_2$, —$(CH)_2Ar$, or unsubstituted or substituted 5-10 membered carbocyclic ring;

$R_5$ is ($C_1$-$C_6$) alkyl;

n is 0, 1, 2 or 3, or a pharmaceutically acceptable salt thereof.

2. The compound according to claim 1, wherein R$_3$ is:

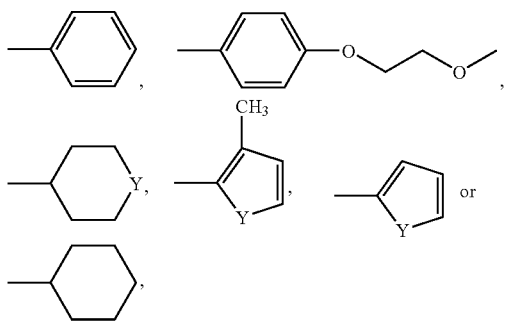

wherein Y is O or S.

3. The compound according to claim 1, wherein X is O.
4. The compound according to claim 1, wherein X is S.
5. The compound according to claim 1, wherein R$_4$ is substituted phenyl which is phenyl mono-, di- or tri-substituted with a group independently selected from the group consisting of halogen, (C$_1$-C$_6$) alkyl, (C$_1$-C$_6$) alkoxy, —O(CH)(CH$_3$)$_2$, —CF$_3$, —O(CH$_2$)$_n$CH$_3$, —OCF$_3$, —SCH$_3$, —SO$_2$CH$_3$, and —NO$_2$.
6. The compound according to claim 1, wherein the compound is benzoic acid N'-[2-(5-fluoro-2'-methoxy-biphenyl-2-yloxy)-acetyl]-N'-isopropyl-hydrazide.
7. The compound according to claim 1, wherein the compound is benzoic acid N'-[2-(5,2'-difluoro-biphenyl-2-yloxy)-acetyl]-N'-isopropyl-hydrazide.
8. The compound according to claim 1, wherein the compound is benzoic acid N'-[2-(5-fluoro-2'-methylsylfanyl-biphenyl-2-yloxy)-acetyl]-N'-isopropyl-hydrazide.
9. The compound according to claim 1, wherein the compound is benzoic acid N'-[2-(5-fluoro-2'-nitro-biphenyl-2-yloxy)-acetyl]-N'-isopropyl-hydrazide.
10. The compound according to claim 1, wherein the compound is benzoic acid N'-[2-(5-fluoro-2'-isopropoxy-biphenyl-2-yloxy)-acetyl]-N'-isopropyl-hydrazide.
11. The compound according to claim 1, wherein the compound is benzoic acid N'-[2-(2'-ethyl-5-fluoro-biphenyl-2-yloxy)-acetyl]-N'-isopropyl-hydrazide.
12. The compound according to claim 1, wherein the compound is benzoic acid N'-[2-(5-fluoro-2'-propoxy-biphenyl-2-yloxy)-acetyl]-N'-isopropyl-hydrazide.
13. The compound according to claim 1, wherein the compound is benzoic acid N'-[2-(2'-methoxycarbonyl-5-fluoro-biphenyl-2-yloxy)-acetyl]-N'-isopropyl-hydrazide.
14. The compound according to claim 1, wherein the compound is benzoic acid N'-[2-(2'-ethoxy-5-fluoro-biphenyl-2-yloxy)-acetyl]-N'-isopropyl hydrazide.
15. The compound according to claim 1, wherein the compound is benzoic acid N'-[2-(5-fluoro-2'-isopropyl-biphenyl-2-yloxy)-acetyl]-N'-isopropyl-hydrazide.
16. The compound according to claim 1, wherein the compound is benzoic acid N'-[2-(2'-ethyl-3,5-difluoro-biphenyl-2-yloxy)-acetyl]-N'-isopropyl-hydrazide.
17. The compound according to claim 1, wherein the compound is benzoic acid N'-[2-(5-methyl-2'-trifluoro-biphenyl-2-yloxy)-acetyl]-N'-isopropyl hydrazide.
18. The compound according to claim 1, wherein the compound is benzoic acid N'-[2-(4,5-difluoro-2'-trifluoromethoxy-biphenyl-2-yloxy)-acetyl]-N'-isopropyl hydrazide.

19. The compound according to claim 1, wherein the compound is benzoic acid N'-[2-(3,5-difluoro-2'-trifluoromethoxy-biphenyl-2-yloxy)-acetyl]-N'-isopropyl hydrazide.
20. The compound according to claim 1, wherein the compound is cyclohexanecarboxylic acid N'-[2-(5-fluoro-2'-trifluoromethoxy-biphenyl-2-yloxy)-acetyl]-N'-isopropyl-hydrazide.
21. The compound according to claim 1, wherein the compound is thiophene-2-carboxylic acid N'-[2-(5-fluoro-2'-trifluoromethoxy-biphenyl-2-yloxy)-acetyl]-N'-isopropyl hydrazide.
22. A method for the treatment of obesity, type II diabetes or metabolic syndrome in a patient in need thereof, which comprises administering to said patient a therapeutically effective amount of a compound of the formula (I):

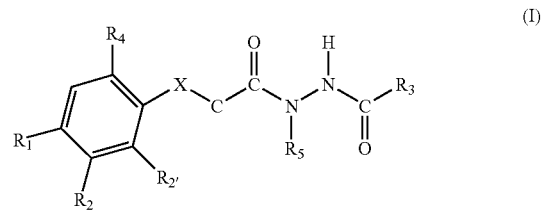

wherein:

X is O or S;

R$_1$ is hydrogen, halogen, (C$_1$-C$_6$)alkyl or cyano;

R$_2$, R$_{2'}$ are independently of each other H or halogen;

R$_3$ is unsubstituted phenyl, substituted phenyl with a group independently selected from the group consisting of halogen, (C$_1$-C$_6$) alkyl, NH(CH$_2$)$_n$CH(CH$_3$)$_2$, or —O(CH$_2$)$_n$OCH$_3$, unsubstituted saturated, unsaturated or partially saturated heterocycyl which is a 5- or 6-membered heteroaromatic ring connected by a ring carbon atom which has from 1 to 3 hetero ring atoms selected from the group consisting of S, N and O, substituted saturated, unsaturated or partially saturated heterocycyl substituted with (C$_1$-C$_6$) alkyl, or substituted or unsubstituted 5-10-membered carboxylic ring;

R$_4$ is branched or unbranched (C$_2$-C$_6$) alkyl, unsubstituted phenyl, substituted phenyl which is phenyl mono-, di- or tri-substituted with a group independently selected from the group consisting of halogen, (C$_1$-C$_6$) alkyl, (C$_1$-C$_6$) alkoxy, —O(CH)(CH$_3$)$_2$, —CF$_3$, —O(CH$_2$)$_n$CH$_3$, —OCF$_3$, —SCH$_3$, —SO$_2$CH$_3$, —NO$_2$, —(CH)$_2$Ar, or unsubstituted or substituted 5-10 membered carboxylic ring;

R$_5$ is (C$_1$-C$_6$) alkyl;

n is 0, 1, 2 or 3, or a pharmaceutically acceptable salt thereof.

23. The method according to claim 22, wherein said therapeutically effective amount of said compound is in an amount of from about 10 mg to about 1000 mg per day.
24. A pharmaceutical composition comprising a compound or a pharmaceutically acceptable salt or ester thereof according to claim 1, and a pharmaceutically acceptable carrier.

* * * * *